United States Patent [19]

Phillips et al.

[11] Patent Number: 5,196,039
[45] Date of Patent: Mar. 23, 1993

[54] APPARATUS AND METHOD OF MULTI-DIMENSIONAL CHEMICAL SEPARATION

[75] Inventors: John B. Phillips, Cabondale, Ill.; Zaiyou Liu, Provo, Utah

[73] Assignee: Southern Illinois University at Carbondale, Carbondale, Ill.

[21] Appl. No.: 846,330

[22] Filed: Mar. 6, 1992

Related U.S. Application Data

[63] Continuation-in-part of Ser. No. 647,790, Jan. 30, 1991, Pat. No. 5,135,549.

[51] Int. Cl.$^5$ .............................................. B01D 15/08
[52] U.S. Cl. .......................................... 55/67; 55/197; 55/386; 210/656; 210/198.2
[58] Field of Search ............... 55/18, 20, 67, 197, 55/208, 386; 73/23.22, 23.26, 61.1 C; 210/656, 198.2

[56] References Cited

U.S. PATENT DOCUMENTS

| | | | |
|---|---|---|---|
| 2,398,818 | 4/1946 | Turner | 55/197 |
| 2,416,482 | 2/1947 | Holmes | 55/197 |
| 3,043,127 | 7/1962 | De Ford et al. | 55/67 X |
| 3,057,183 | 10/1962 | De Ford | 55/197 X |
| 3,063,286 | 11/1962 | Nerheim | 55/197 X |
| 3,150,516 | 9/1964 | Linnenbom et al. | 55/197 X |
| 3,156,548 | 11/1964 | Perry | 55/197 |
| 3,225,520 | 12/1965 | Burow | 55/197 X |
| 3,225,521 | 12/1965 | Burow | 55/197 X |
| 3,236,603 | 2/1966 | Durrett et al. | 55/197 X |
| 3,449,938 | 6/1967 | Giddings | 55/67 X |
| 3,782,078 | 1/1974 | Jerpe | 55/197 |
| 3,881,892 | 5/1975 | Gehrke et al. | 55/197 X |
| 3,920,420 | 11/1975 | Valentin et al. | 55/197 X |
| 3,926,589 | 12/1975 | Klementi et al. | 55/67 |
| 4,019,863 | 4/1977 | Jenkins et al. | |
| 4,554,436 | 11/1985 | Chlosta et al. | 55/386 X |
| 4,719,011 | 1/1988 | Shalon et al. | 55/386 X |
| 4,726,822 | 2/1988 | Cates et al. | 55/197 X |
| 4,774,190 | 9/1988 | Weiss | 55/67 X |
| 4,923,486 | 5/1990 | Rubey | 55/197 X |
| 4,935,145 | 6/1990 | Cortes et al. | 55/67 X |
| 5,005,399 | 4/1991 | Holtzclaw et al. | 73/23.39 |

FOREIGN PATENT DOCUMENTS

| | | | |
|---|---|---|---|
| 2629048 | 1/1977 | Fed. Rep. of Germany | 55/197 |
| 2823445 | 12/1979 | Fed. Rep. of Germany | 55/197 |
| 59-221664 | 12/1984 | Japan | 55/67 |
| 62-190464 | 8/1987 | Japan | 55/67 |

OTHER PUBLICATIONS

J. Q. Walker et al., *Analytical Chemistry*, vol. 42, No. 13, Nov. 1970, pp. 1652–1654.
W. J. Baker et al., *Control Engineering*, Jan. 1961, pp. 77–81.
P. D. Koons et al., *Hydrocarbon Processing & Petroleum Refiner*, Apr. 1963, vol. 42, No. 4, pp. 133–135.
S. A. Greene et al., *Analytical Chemistry*, vol. 28, No. 9, Sep. 1956, pp. 1369 & 1370.
J. S. Lewis et al., *Analytical Chemisry*, vol. 28, No. 9, Sep. 1956, pp. 1370 & 1371.

(List continued on next page.)

*Primary Examiner*—Robert Spitzer
*Attorney, Agent, or Firm*—Watson, Cole, Grindle & Watson

[57] ABSTRACT

A practical device and method of performing comprehensive multi-dimensional chemical separation using a first dimension of a two-dimensional chromatograph to generate a chromatogram in a time comparable to or even faster than common practice while the second dimension generates multiple chromatograms each in a time comparable to the fastest prior art chromatography. The transfer of sample portions from the first dimension to the second dimension is by any one of several sample stream modulation techniques. These techniques accumulate portions of sample between the first and the second dimensions transferring them as very sharp concentration pulses analogous to fast injections, without loss of sample and with a substantial improvement in sensitivity.

76 Claims, 8 Drawing Sheets

OTHER PUBLICATIONS

"Automated Instrumentation for Comprehensive Two-Dimensional High-Peformance Liquid Chromatography of Proteins", M. Bushey et al., *Anal. Chem.* 1990, vol. 62, pp. 161-167.

"Automated Instrumentation for Comprehensive Two-Dimensional High-Performance Liquid Chromatography/Capillary Zone Electrophoresis", M. Bushey et al., *Anal. Chem.* 1990, vol. 62, pp. 978-984.

Supelco Advertisment, p. 3. (date and source unknown).

"Thermal Modulation Boosts GC Sensitivity", *C&EN* Jan. 14, 1985, pp. 62-64.

"Thermal Desorption Modulation as a Replacement for Sample Injection in Very-Small-Diameter Gas Chromatography Capillary Columns", J. Phillips et al., *Journal of Chromatographic Science* 1986, vol. 24, pp. 396-399.

"Multidimensional Gas Chromatography", W. Bertsch, *Journal of High Resolution Chromatography*, Univesity of Alabama, pp. 74-144.

"Two Dimensional Multiplex Gas Chromatography", D. Palovic et al., *1983 Pittsburgh Conference Book of Abstracts*, No. 797.

"Two Dimensional Multiplex Gas Chromatography", D. Carney, Southern Illinois University, May 1983.

"Comprehensive Two-Dimensional Gas Chromatography Using an On-Column Thermal Modulator Interface", Z. Liu et al., *Journal of Chromatographic Science*, 1991, vol. 29, pp. 227-231.

"Large-Volume Sample Introduction Into Narrow-Bore Gas Chromatography Columns Using Thermal Desorption Modulation and Signal Averaging", Z. Liu et al., *Journal of Microcolumn Separations*, 1990, vol. 2, No. 1, pp. 33-40.

"High-Speed Gas Chromatography Using an On-Column Thermal Desorption Modulator", Z. Liu et al., *J. Microcolumn Separations*, 1989, vol. 1, No. 5, pp. 249-256.

"Sample Introduction into a 5-um i.d. Capillary Gas Chromatography Column Using an On-Column Thermal Desorption Modulator", Z. Liu et al., *J. Microcolumn Separations*, 1989, vol. 1, No. 3, pp. 159-162.

"High-Capacity Thermal Desorption Modulators for Gas Chromatography", S. Mitra et al., *Journal of Chromatographic Science*, 1988, vol. 26, pp. 620-623.

"Determination of Activity Coefficients of Binary Liquids by Capillary Gas Chromatography with Thermal Desorption Modulation for Direct Headspace Sampling", M. Zhang et al., *Journal of Chromatography*, 1989, vol. 478, pp. 141-147.

"Multiplex Gas Chromatography by Thermal Modulation of a Fused Silica Capillary Column", J. Phillips et al., *Analytical Chemistry*, 1985, vol. 57, pp.2779-2787.

"Temperature-Controlled High-Speed Microcolumn Liquid Chromatography", K. Jinno, *Analytical Chemistry*, 1985, vol. 57, No. 2, pp. 574-576.

"A Non-Mechanical Chemical Concentration Modulator for Multiplex Gas Chromatography", J. Valentin et al., *Journal of HRC & CC*, 1982, pp. 269-272.

bThermal Desorption Modulation as a Replacement for Sample Injection in Very-Small-Diameter Gas Chromatography Capillary Columns", J. Phillips et al., *Journal of Chromatographic Science*, 1986, vol. 24, pp. 396-399.

"Electrically Heated Cold Trap Inlet System for High--Speed Gas Chromatography", B. Ewels et al., *Anal. Chem.*, 1985, 57, pp. 2774-2779.

"Use of Multiple Dimensions in Analyical Separations", J. Giddings, *Multidimensional Chromatography Techniques and Applications*, H. Cortes, Ed., p. v-27.

"Two-Dimensional Separations", J. Giddings, *Unified Separation Science*, pp. 123-131.

"Two-Dimensional Measurements Involving Chromatography", M. Kaljurand et al., *Computerized Multiple Input Chromatography*, pp. 59-99.

"Analysis of Flue-Cured Tobacco Essential Oil by Hyphenated Analytical Techniques", B. Gordon et al., *Journal of Chromatographic Science*, 1988, vol. 26, pp. 174-180.

"Cryogenic-Focusing, Ohmically Heated On-Column Trap for Capillary Gas Chromatography", S. Springston, *Journal of Chromatography*, 1990, vol. 517, pp. 67-75.

"Multi-Dimensional Chromatography Using On-Line Coupled Microcolumn Liquid Chromatography-Capillary Gas Chromatography for Quantitative Pesticide Residue Analysis", H. Cortes et al., *Analytica Chimica Acta*, 1990, vol. 236, pp. 173-182.

(List continued on next page.)

OTHER PUBLICATIONS

"Design and Performance of a Mass-Flow-Modulated Detector for Gas Chromatography", G. Wells, *Journal of Chromatography*, 1985, vol. 319, pp. 263–272.

"Advances in Two-Dimensional GC with Glass Capillary Columns", E. Anderson, *Journal of High Resolution Chromatography & Chromatography Communications*, 1979, vol. 2, pp. 335–338.

"Methods in High Resolution Gas Chromatography. Two-Dimensional Techniques", W. Bertsch, *Journal of High Resolution Chromatography & Chromatography Communications*, Aug. 1978, pp. 85–90.

"Methods in High Resolution Gas Chromatography. Two-Dimensional Techniques", W. Bertsch, *Journal of High Resolution Chromatography & Chromatography Communications*, Dec. 1978, pp. 289–299.

"Concepts and Comparisons in Multidimensional Separation", J. Giddings, *Journal of High Resolution Chromatography & Chromatography Communications*, 1987, vol. 10, pp. 319–323.

"Gas Chromatographic Response as a Function of Sample Input Profile", Reilley et al., *Analytical Chemistry*, Sep. 1962, vol. 34, No. 10, pp. 1198–1213.

"Methods in High Resolution Gas Chromatography. Two-Dimensional Techniques", W. Bertsch, *Journal of High Resolution Chromatography & Chromatography Communications*, Oct. 1978, pp. 187–194.

"Multidimensional Separation of Isomeric Species of Chlorinated Hydrocarbons Such as PCB, PCDD, and PCDF", G. Schomburg et al., *Journal of High Resolution Chromatography & Chromatography Communications*, 1985, vol. 8, pp. 395–400.

"Coupling of High-Performance Liquid Chromatogaphy with Capillary Gas Chromatography", K. Grob, Jr., *Journal of Chromatography*, 1984, vol. 295, pp. 55–61.

"Multidimensional Gas Chromatography with Electron Capture Detection for the Determination of Toxic Congeners in Polychlorinated Biphenyl Mixtures", J. Duinker et al., *Anal. Chem.*, 1988, vol. 60, pp. 478–482.

"Therm. Mod. for Sample Intro. Into Ultra-Sm. Diameter Cap. Clmns. in GC", J. Phillips et al., 11th Int'l Symp. on Cap. Chrom., May 1990.

"Anal. of Explosives Using High-Sp. Gas Chrom. with Chemilum. Detection", D. Rounbehler et al., 1st In. Symp. on Explosive Detection Technology, Nov. 1991.

"High-Sp. Gas Chrom. Anal. of a Sim. Process Stream Using On-Col. Therm. Desorption Mod. for Sample Preconcent. and Intro.", Z. Liu et al., *J. Chrom. Sci.*, vol. 28, Nov. 1990.

First - isothermal
Second - all at one temperature

First - isothermal
Second - temperature incremented

First - temperature programmed
Second - all at one temperature

First - temperature programmed
Second - temperature incremented

A Two-Dimensional Gas Chromatogram
Demonstrating Orthogonality of the Separation Temperature program: 70 °C for 45 seconds, then 43°C per minute
First column: Quadrex 007 methyl 5% phenyl, 11m
Second column: Quadrex 007 OV-1701, 1.4m
Modulator: 24 cm two-stage on second column

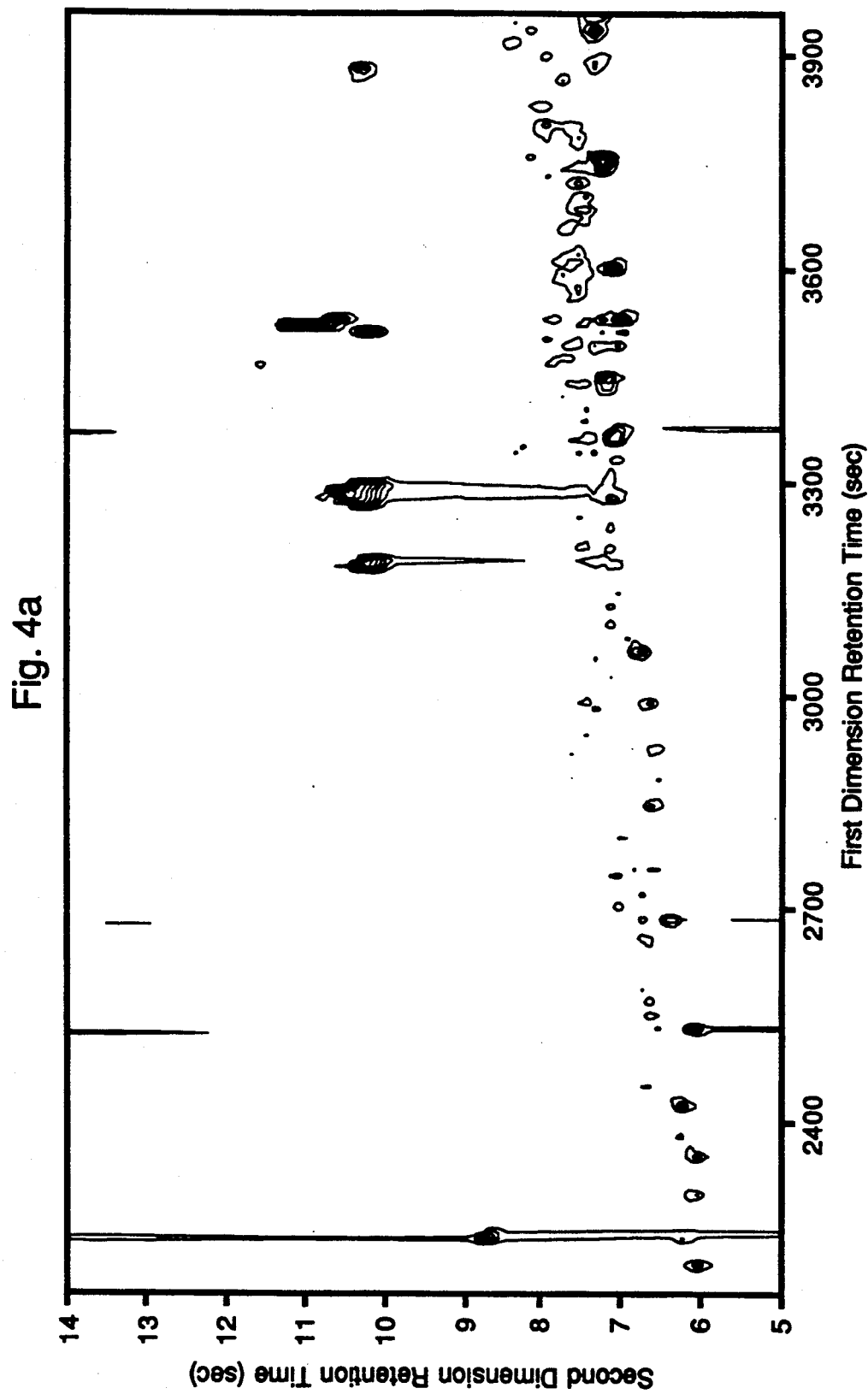

APPARATUS AND METHOD OF MULTI-DIMENSIONAL CHEMICAL SEPARATION

This application is a continuation-in-part of application Ser. No. 07/647,790, filed Jan. 30, 1991, now U.S. Pat. No. 5,135,549.

BACKGROUND OF THE INVENTION

This invention relates to chemical separation methods, in particular to chromatographic and electrophoretic methods.

Prior Art Two-Dimensional Chromatography

In one class of chromatography, referred to as two-dimensional chromatography, two differing chemical separation mechanisms are applied in sequence to separate a sample. In planar chromatography, for example, two-dimensional separation is achieved by first separating the sample in one direction using one mechanism to give a first chromatogram dispersed along a line and then separating this first chromatogram in an orthogonal direction using a second and different mechanism to disperse substances over the plane. To be separated from other components of the sample, a substance need be separated in only one or the other of the two directions. The first separation defines a first dimension of chromatography and the second defines a second dimension of chromatography.

Two-dimensional chromatography can also be achieved with coupled columns rather than a planar chromatographic bed. In this group of techniques, a sample is first separated in one column using one chemical mechanism to give a first chromatogram. A portion of the sample taken from this first chromatogram is introduced to a second column where it is separated using a second chemical mechanism. In such a system, the sample is not dispersed over a physical plane, but in certain respects the separation is analogous to two-dimensional planar chromatography. The two different separation mechanisms define a first dimension of chromatography and a second dimension of chromatography. To be separated from other components of the sample, a substance need be separated on only one or the other of the two dimensions of chromatography.

To provide a two-dimensional separation, two columns cannot be coupled so that all sample simply flows from the first column into the second. A direct connection such as this would result only in a one-dimensional separation. Some mechanism must be provided between the two columns to sample the first chromatogram into the second column.

In two-dimensional gas chromatography, column to column sample transfer is commonly referred to as "heart-cutting" because a small portion, or "heart-cut", of the first separation is transferred to the second column. Heart-cutting is often used to determine target compounds in complex mixtures. The first column separates the desired component from most of the sample but, due to insufficient resolving power, cannot separate it from all other mixture components. The portion of sample transferred to the second column is a much simpler mixture which can then be separated on the second column to give the desired component as an isolated band. The separation mechanism in the second column must differ from that of the first column. Otherwise, mixture components which overlap the desired component in the first chromatogram will also overlap in the second column. Most prior art multi-dimensional separations employing coupled columns are heart-cutting techniques.

Heart-cutting techniques have the disadvantage of being incomplete in the sense that only a small portion of the sample is submitted to the second separation. Generally, only one heart-cut is transferred to the second column. The majority of the sample substances do not pass through the second column and are not subjected to a two-dimensional separation. This deficiency is best visualized by comparing heart-cutting techniques to planar chromatography. The second dimension of a heart-cut chromatogram then corresponds to a single second dimension slice or portion of the planar chromatogram. The rest of the theoretically available two-dimensional chromatogram, a two-dimensional data space, is not generated.

Some more sophisticated coupled column techniques have been described in which more than one portion of sample is taken from the first chromatogram and transferred to the second column. These multiple heart-cuts can all be taken either from a single first dimension chromatogram or each from one of a series of first dimension chromatograms as in the report: Bert M. Gordon, Mary S. Uhrig, Michael F. Borgerding, Henry L. Chung, William M. Coleman, III, James F. Elder, Jr., J. A. Giles, Dennis S. Moore, Charles E. Rix, and Earl L. White. Analysis of Flue-Cured Tobacco Essential Oil by Hyphenated Analytical Techniques. *J. Chromatogr. Sci.* 26: 174–180 (1988). These techniques come closer to complete coverage of the retention plane, but are still incomplete in the sense that the first dimension separation cannot be reconstructed from the set of second dimension chromatograms. Alternately, the retention plane is incompletely developed. A severe disadvantage of this method is time and labor involved in repeating.

Comprehensive two-dimensional chromatography is a coupled column technique in which the number of portions of sample transferred from the first column to the second is sufficient to substantially preserve the first dimension chromatogram. This prior art is described in the article: Michelle M. Bushey and James W. Jorgenson. Automated Instrumentation for Comprehensive Two-Dimensional High-Performance Liquid Chromatography of Proteins. *Anal. Chem.* 62: 161–167 (1990). A large difference in speed between the first and second dimensions of chromatography is required to make two-dimensional chromatography comprehensive. Bushey and Jorgenson achieve this speed difference by greatly decreasing the first column's speed. The time required for generation of a comprehensive two-dimensional chromatogram is then substantially more than that required for a one-dimensional chromatogram or for a heart-cut chromatogram.

One of the central issues of two-dimensional chromatography is "orthogonality". The concept of orthogonality in multi-dimensional separations has not been precisely defined. It is generally understood to mean separation by a pair of methods whose mechanisms are independent of each other so that the distribution of substances in one dimension is uncorrelated with the distribution of substances in another dimension. In prior art comprehensive two-dimensional chromatography, the chemical separation mechanisms of each of the two dimensions are made different by coupling different varieties of chromatography. For example, Bushey and Jorgenson coupled ion exchange liquid chromatography with size exclusion liquid chromatography in order to generate "orthogonal" two-dimensional chromatograms. They also reported a comprehensive two-dimensional separation combining liquid chromatography with electrophoresis in the article: M. M. Bushey and J. W. Jorgenson. Automated Instrumentation for Comprehensive Two-Dimensional High-Performance Liquid Chromatography/Capillary Zone Electrophoresis. *Anal. Chem.* 62: 978–984 (1990).

A disadvantage of prior art comprehensive two-dimensional chromatography is the need to couple two different chemical separation mechanisms in order to obtain orthogonal separation. It is widely assumed, and rightly so, that separation mechanisms are usually quite different for different varieties of chromatography and for combinations of chromatographic with non-chromatographic separation techniques. Combining two such different separation methods in a comprehensive two-dimensional technique is usually sufficient to obtain orthogonality. It is further assumed that combining two such different separation methods in a comprehensive two-dimensional technique is necessary to obtain orthogonality. This second assumption is false.

Two-dimensional separations are discussed in theory by Giddings in *Unified Separation Science* Wiley (1991) pages 122–137.

Prior Art Sample Modulation Techniques

Thermal methods of sample introduction include cold trap and single-stage thermal modulators. In both of these, sample substances are retained within the device at a relatively cold temperature and released as a concentration pulse at a relatively hot temperature, the heat being commonly applied by passage of electrical current through the device or through a resistive film applied to the device An adsorptive material similar or identical to a chromatographic stationary phase may be present within the device. Cold traps are designed to trap an entire sample and hold it for an indefinite period of time. A typical cold trap design is described in the article: A. van Es, J. Janssen, C. Cramers, and J. Rijks. Sample Enrichment in High Speed Narrow Bore Capillary Gas Chromatography. *HRC & CC* 11: 852–857 (1988). Single-stage thermal modulators are designed to hold only a portion of a sample for only a limited period of time. A typical single-stage thermal modulator design is described in the article: Ziyou Liu and John B. Phillips. Large Volume Sample Introduction into Narrow-Bore Gas Chromatography Columns Using Thermal Desorption Modulation and Signal Averaging. *J. Microcolumn Separations* 2: 33–40 (1990).

Prior art cold traps have the disadvantage of requiring a large and fast temperature change. Both cold traps and single-stage thermal modulators when used with continuously flowing sample streams, allow some sample to pass through unmodulated.

A cold trap device heated by passing electric current through a thin conductive film applied externally to a fused silica capillary gas chromatographic column is described in the article: Stephen R. Springston. Cryogenic-Focusing Ohmically Heated On-Column Trap for Capillary Gas Chromatography. *J. Chromatogr.* 517: 67–75 (1990).

Prior Art Retention Gradient Techniques

Thermal gradients have been established along gas chromatographic columns for the purpose of forming a retention gradients. A thermal gradient method designed for high-speed gas chromatography is described in the patent: Marion H. Cates and William E. Skillman, III. Fast Response Thermochromatographic Capillary Columns. U.S. Pat. No. 4,726,822 (1988). A thermal gradient method using gradients in both distance along the column and time is described in the patent: Wayne A. Rubey. Gas Chromatography Methods and Apparatus. U.S. Pat. No. 4,923,486 (1990).

Prior art retention gradient methods have not been applied to the improvement of comprehensive multi-dimensional chromatographic techniques.

Prior Art Two-Dimensional Electrophoresis

Electrophoresis has been used in two-dimensional configurations in combination with other chemical separation techniques, particularly with liquid chromatography. Electrophoresis on a planar bed is well known in combination with thin layer chromatography. Electrophoresis in a capillary tube is a more recent development, but it too has been combined with liquid chromatography in a two-dimensional coupled-column technique. A very high-speed capillary electrophoresis method connected to a liquid chromatography in a comprehensive two-dimensional instrument design is described in the article: M. M. Bushey and J. W. Jorgenson. Automated Instrumentation for Comprehensive Two-Dimensional High-Performance Liquid Chromatography: Capillary Zone Electrophoresis. *Anal. Chem.* 62: 978–984 (1990).

Prior art comprehensive two-dimensional instruments involving electrophoresis as one of the dimensions have always required a separation technique other than electrophoresis for the other dimension.

SUMMARY OF THE INVENTION

The present invention provides a practical means of performing comprehensive multi-dimensional chemical separation.

The first dimension of a two-dimensional chromatograph generates a chromatogram in a time comparable to or even faster than common practice while the second dimension generates multiple chromatograms each in a time comparable to the fastest prior art chromatography. The transfer of sample portions from the first dimension to the second dimension is by any one of several sample stream modulation techniques. These techniques accumulate portions of sample between the first and the second dimensions transferring them as very sharp concentration pulses analogous to fast injections, usually without loss of sample and usually with a substantial improvement in sensitivity.

The present invention provides a new thermal modulation technique to accumulate and focus, refocus, and then accelerate a concentration pulse in a carrier stream.

The present invention permits the use of similar chromatographies or separation techniques for both dimensions of chemical separation without loss of orthogonality and greatly simplifies the interface between dimensions. Small differences in retention mechanism are sufficient to generate orthogonal separation when retention in the second dimension of chromatography is adjusted as a function of progress of the first dimension of chromatography.

BRIEF DESCRIPTION OF THE DRAWINGS

The present invention may be more fully understood with reference to the accompanying drawings herein, where:

FIGS. 4a-4e together comprise a comprehensive two-dimensional gas chromatogram, divided into five sequential time periods of partially evaporated gasoline sample.

DETAILED DESCRIPTION OF THE INVENTION

Structure of a Comprehensive Multi-Dimensional Chromatograph

Figure 1:
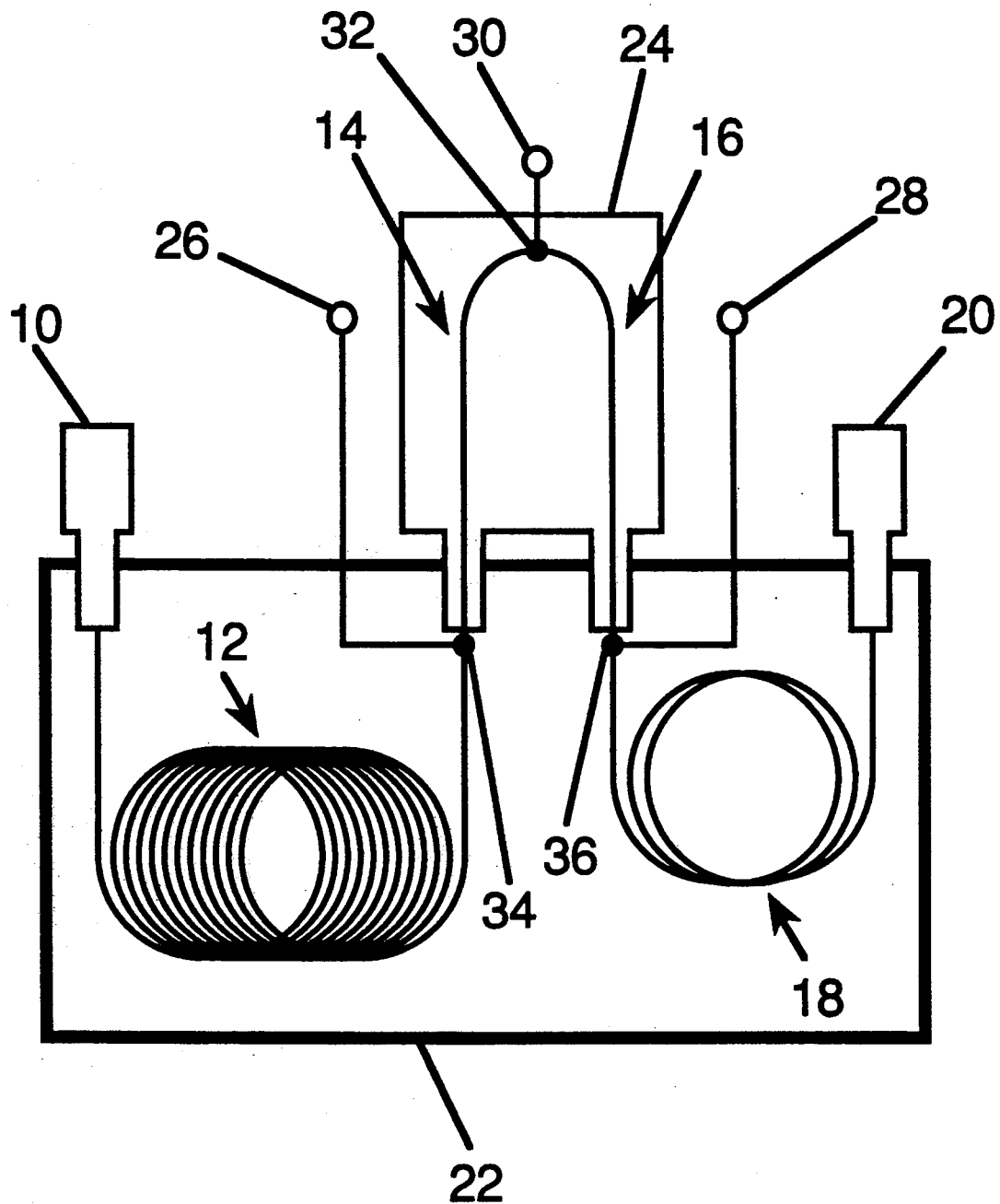
FIG. 1. is a schematic diagram of a comprehensive two-dimensional chromatograph according to the present invention.

In FIG. 1, two chromatographic columns are connected in series so that chromatographic mobile phase and sample flow from the first to the second through a thermal modulator. The two columns may be of conventional type, either packed or open tubular, and may be prepared in separate pieces of tube or in a single tube. If the two columns are prepared in separate pieces of tube, the pieces may be connected by any fitting or technique that does not degrade the separation produced by the first column as separated bands flow from the first column into the second with the chromatographic mobile phase. If the two columns are prepared in a single tube, as illustrated in FIG. 1, separated bands flow directly from the first column 12 through modulator inlet stage 14 and outlet stage 16 to the second column 18 with the chromatographic mobile phase. The two chromatographic columns are placed in a temperature controlled enclosure 22 and the two modulator stages are placed in a separate temperature controlled enclosure 24.

Sample input to the first column of the device shown in FIG. 1 may be by any sample injection device or means well known in the art such as a syringe injection through an injection port 10. The outlet of the sample input device connects to the inlet of the first column 12. Alternatively, a thermal modulator may be connected between the outlet of the sample injection device and the inlet of the first column. Also alternatively, a thermal modulator may be connected between a continuously flowing sample stream and the inlet of the first column without a sample injection device.

The outlet of the second column may connect to the inlet of a chromatographic detector 20. In some embodiments, the outlet of the second column may connect to a sample collection device or to both a chromatographic detector and a sample collection device connected either in series or parallel. The detector may be of any type appropriate to the sample and to the second column. In some embodiments, the detector must have a short response time to transduce fast chromatographic bands.

A modulator is placed near the junction between the first and second columns. The modulator may be a device separate from both columns and connected between them so that mobile phase and sample flow from the outlet of the first column, through the modulator, and into the inlet of the second column. Alternatively, the modulator may be a thermal modulator and may be prepared on-column as an integral part of either the first or the second column or be prepared on-column spanning the junction between both columns.

In the embodiment of FIG. 1, the thermal modulator inlet stage 14 accumulates sample substances emerging from the first column 12 and hold them for a period of time. An electric current is applied between the inlet stage electrical contacts 26 and 30 to heat the inlet stage of the thermal modulator releasing sample substances. These sample substances are carried by a mobile phase to the outlet stage 16 where they are refocussed and held until the inlet stage cools sufficiently to again hold sample substances. An electric current is then applied between the outlet stage electrical contacts 28 and 30 to heat the outlet stage of the thermal modulator. The electrical contact 30 is connected to the thermal modulator at the junction 32 between inlet and outlet stages and serves both stages. Electrical contacts 26 and 28 are connected to the thermal modulator at the inlet end 34 and the outlet end 36.

Both first and second columns contain chromatographic stationary phases. In some embodiments, the thermal modulator also contains a chromatographic stationary phase. In some embodiments, the stationary phases in the two columns differ chemically from each other. There may, however, be one chemically uniform stationary phase in both columns with a difference in retention mechanism between the first and the second column being due to a difference in temperature at which sample substances propagate along the first and second columns.

One or more additional column and one or more additional modulator may be inserted in series with the first and second columns such that columns and modulators alternate in the series.

Operation of a Comprehensive Multi-Dimensional Chromatograph

Broadly, in this method, multiple second dimension chromatograms are generated during the time period of a first dimension chromatogram. Second dimension chromatograms are generated at high speed and high repetition rate using a modulator at the junction between the first and second dimensions of chromatography. The set of second dimension chromatograms may be displayed in a three-dimensional manner with a retention parameter of the first column comprising one axis, a retention parameter of the second column comprising a second axis and signal intensity comprising a third axis.

In operation, the first column provides a first separation of the sample and the second column provides a second and different separation of the sample. The difference in separation may be due to a difference in stationary phase, a difference in mobile phase, or a difference in environment. The phrase "first dimension of chromatography" is defined to include all the features in or associated with the first column that determine the separation. These features include the stationary phase in the first column, the mobile phase passing through the first column, and the environment of the first column. Similarly, the phrase "second dimension of chromatography" is defined to include the stationary phase in the second column, the mobile phase passing through the second column, and the environment of the second column.

To operate the comprehensive two-dimensional chromatograph, a sample is injected into the first dimension of chromatography to generate a first separation of the sample into a series of bands dispersed during a time period. This is a first dimension chromatogram and is similar to a chromatogram that could be obtained from a conventional one-dimensional chromatograph operated under the same conditions. Each band in the first dimension chromatogram contains one or more substances and may be separated from all adjacent bands or partially overlapping with one or more adjacent bands.

The modulator accumulates portions of the sample from the first dimension chromatogram and transfers them to the second dimension in the form of concentration pulses. Mobile phase flows from the first column to the second column through the modulator. The modulator may be any one of a number of devices. In one embodiment with a gas mobile phase and a thermal modulator, the modulator is relatively cool during the accumulation phase of its operation and relatively warm during concentration pulse generation. Each concentration pulse is analogous to a chromatographic injection and generates a second dimension chromatogram. Each second dimension chromatogram is similar to a chromatogram that could be obtained from a fast one-dimensional column chromatograph operated under the same conditions. The modulator may be a single-stage thermal modulator or a multi-stage thermal modulator. Alternatively, the modulator may be a cold trap or an injection valve with a sample loop.

Multiple second dimension chromatograms are generated during the time period of the first dimension chromatogram. In one embodiment, this is achieved by making each second dimension chromatogram substantially faster than the first dimension chromatogram. To make two-dimensional chromatography comprehensive, it is sufficient that the two dimensions differ substantially in speed. If the second dimension is substantially faster than the first, then multiple, such as ten or more, second dimension chromatograms can be generated during the time period of the first dimension chromatogram. However, for two-dimensional chromatography to be both comprehensive and be of practical value in applications in which it is in competition with one-dimensional or heart-cutting chromatography, the overall rate of information production should be significantly greater than a rate obtainable with the competing chromatographic methods. Generating second dimensional chromatograms at a rate greater than one every thirty seconds increases the information production rate so that comprehensive two-dimensional chromatography is useful.

It is not necessary that a second dimension chromatogram be complete before the next portion of sample is transmitted to the second dimension but only that chromatograms not overlap at the end of the second dimension to a degree which prevents interpretation of the data. Two or more separations may be in progress in the second dimension of chromatography at the same time. The second dimension separation time period may be less than the maximum retention time of substances in the second dimension of chromatography.

In the present invention, the first dimension chromatogram is sampled onto the second dimension of chromatograph with fidelity. The term "fidelity" here means that the first separation is maintained upon transfer to and transmission through the second dimension of chromatography. This is analogous to transmission of an electronic signal through a communication channel in that the channel capacity should be sufficient to transmit the desired information. In the case of comprehensive two-dimensional chromatography, the rate of second dimension chromatogram repetition should be sufficient to transmit the first separation through the second dimension to the two-dimensional chromatogram. Also analogous to transmission through a communication channel, the channel capacity is not required to be any greater than that required to transmit the desired first separation. The first separation is transmitted through the second dimension, but other features or details of the first chromatogram such a band shape need not be transmitted accurately unless these other features or details contain desired information. To transmit substantially all first dimension chromatographic information, including band shape information, through the second dimension of chromatography, a minimum of five second dimension chromatograms are required during a time equal to the duration of a band eluting from the first dimension of chromatography. However, to transmit only the first dimension separation through the second dimension of chromatography, a lower rate of second dimension chromatograms is acceptable. The acceptable rate may be less than a single second dimension chromatogram per first dimension band duration if the first dimension resolution is greater than that required to obtain the separation of interest. The first dimension chromatogram is transmitted with fidelity if the desired first dimension separation is maintained through the second dimension of chromatography. To transmit band amplitude (sample quantitation) information through the second dimension of chromatography, second dimension chromatograms need be generated at a rate no faster than that needed to maintain the first dimension separation if the modulator accumulates sample throughout the second dimension sampling period. If the modulator is does not accumulate sample throughout the second dimension sampling period, then second dimension chromatograms may be required at a rate fast enough to transmit at least approximate first dimension band shape information through the second dimension.

A concise definition "fidelity" as it relates to this invention is: the maintenance of the first separation in a comprehensive two-dimensional chromatogram created from the multiplicity of the final series of bands, the comprehensive two-dimensional chromatogram being a separation of the sample into a set of bands dispersed on a retention plane, the retention plane being a vectorial space of dimension two and spanned by the first and final separation time periods.

The set of second dimension chromatograms generated during the period of the first dimension chromatogram forms a comprehensive two-dimensional chromatogram in which both separations in both dimensions of chromatography are represented.

The sample is separated into a set of bands dispersed on a retention plane analogous to the plane of a planar chromatography. This retention plane is a two-dimensional vectorial space spanned by the first and second separation time periods. The chromatographic data is conveniently displayed as a three dimensional plot in which retention in the first dimension forms on axis, retention in the second dimension forms a second axis, and signal intensity forms a third axis. It should be understood, however, that it is the comprehensive two-dimensional nature of the separation which is fundamental. The data need not be displayed in any particular way.

The present invention may be generalized to include more than two dimensions of chromatography. A first dimension of chromatography, a final dimension of chromatography, and a modulator at the junction are required for the invention. An additional dimension or dimensions of chromatography and an additional modulator or modulators may be placed serially between the first and final dimensions of chromatography to provide additional dimensions of separation.

From the foregoing discussion it is clear that one embodiment of the invention may be described as: a method of chemical separation comprising one or more portion of tube forming one or more chromatographic column, the method further comprising the steps of: (a) injecting a sample composed of two or more substances into a first dimension of chromatography; (b) carrying the sample along the first dimension of chromatography in a direction so as to cause a first separation of the sample into a first series of bands dispersed during a first separation time period, each band of the first series of bands being composed of one or more substance and being either separated from or partially overlapping with one or more other band in the first series of bands; (c) accumulating a portion of the sample in a modulator positioned between the first dimension of chromatography and a final dimension of chromatography disposed in serial relationship with the first dimension of chromatography; (d) transmitting the portion of the sample from the modulator as a concentration pulse into the final dimension of chromatography; (e) carrying the portion of the sample along the final dimension of chromatography in a direction so as to cause a final separation of the portion of the sample into a final series of bands dispersed during a final separation time period; and (f) repeating steps (c), (d), and (e) during the first separation time period so as to generate a multiplicity of the concentration pulses, a multiplicity of the final separations and a multiplicity of the final series of bands during a multiplicity of the final separation time periods such that, the concentration pulses are generated at a rate faster than one every thirty seconds, the multiplicity of final separations comprises more than ten final separations of sample injected in step (a), and the first series of bands emerging from the first dimension of chromatography is submitted to and transmitted through the final dimension of chromatography with fidelity.

It is clear from the foregoing discussion that the invention may be generalized to include: the method wherein one or more dimension of chromatography is serially disposed between the first dimension of chromatography and the final dimension of chromatography with two or more junctions created between the dimensions of chromatography, each junction having a prior dimension of chromatography and a subsequent dimension of chromatography such that, at each junction, sample emerges from the prior dimension of chromatography as a series of bands, a multiplicity of portions of the sample are accumulated by an instance of the modulator and are transmitted to the subsequent dimension of chromatography so as to generate a multiplicity of concentration pulses and a multiplicity of subsequent dimension separations with fidelity, fidelity comprising maintenance of all prior dimension separations such that, a comprehensive multi-dimensional chromatogram is created from a multiplicity of a series of bands emerging from the final dimension of chromatography, the comprehensive multi-dimensional chromatogram being a separation of the sample into a set of bands dispersed in a retention space, the retention space being a vectorial space of dimension equal to the multiplicity of dimensions of chromatography and spanned by the separation time periods of the multiplicity of dimensions of chromatography.

From the foregoing discussion it is clear that one embodiment of the invention may be described as: a method of comprehensive two-dimensional chromatography wherein the concentration pulse is transmitted to the final dimension of chromatography before a previous portion of the sample has completely eluted from the final dimension of chromatography and more than one portion of the sample is present in the final dimension of chromatography at one time.

Quantitation of Multi-Dimensional Chromatograms

Multiple final dimension chromatograms emerge from the outlet of the final dimension of chromatography in a continuous flow of chromatographic mobile phase and form a single concatenated and continuous series of bands which may be passed to the inlet of a detector. The detector transduces the series of bands to form an electronic signal which may be digitized for processing in a computer.

One or more of the following operations may be done on the electronic signal or the digitized electronic signal. First, the electronic signal may be displayed as a comprehensive two-dimensional chromatogram with a retention parameter of the first column comprising one axis, a retention parameter of the final column comprising a final axis and signal intensity comprising a third axis. Second, a region occupied by a two-dimensional chromatographic band may be integrated on the two-dimensional plane to give a measure of band volume. And third, the measure of band volume may be corrected for a background offset by subtracting an integral computed over an empty region of the retention plane equal in size to, and located in the general vicinity of, the region occupied by the chromatographic band.

Such a ground offset correction is a particular advantage of comprehensive two-dimensional chromatography. The substantially larger peak capacity of the retention plane in comparison with the retention line of one-dimensional chromatography makes it very likely that regions of the retention plane near the chromatographic band of interest will be truly empty. Having ready access to true baseline improves both precision and accuracy of band altitude and volume determinations.

Orthogonality of Multi-Dimensional Chromatography

A non-orthogonal separation is one in which retentions in one dimension are correlated with those in another dimension. As a result, chromatographic bands will occupy only limited regions of the potentially available retention space. In such a case, the overall peak capacity of the separation system may be substantially less than the arithmetic product of the individual peak capacities of each dimension of separation.

An orthogonal multi-dimensional separation is one in which retentions in each of the dimensions are independent of retentions in every other dimension. Orthogonality is an ideal which may be approached to varying degrees because varying degrees of correlation between retentions are possible.

Orthogonality is important in multi-dimensional separation because the potential peak capacity of a multi-dimensional chromatogram is equal to the product of the peak capacities of the constituent one-dimensional separations. Even with modest individual peak capacities, this product can reach a very large value.

To further elaborate on the concept of orthogonality consider a comprehensive two-dimensional chromatograph could hypothetically be built by coupling an array of secondary columns to the end of a single primary column. The secondary columns are all identical but differ from the primary column in stationary phase. The eluant from the primary column is transferred to the secondary column array by an array of stream switching valves. In this hypothetical instrument enough valves and secondary columns are provided to divide the entire primary column effluent into portions comparable in volume to that occupied by one peak in the primary chromatogram. Secondary chromatograms are generated in parallel and detected by an array of chromatographic detectors. By plotting the set of parallel chromatograms as a series of overlapping traces, as a contour plot, or in some other three-dimensional representation, we could, in principle generate a two-dimensional gas chromatogram. Each substance in this chromatogram would be characterized by two retention times on two different stationary phases.

The Use of Retention Gradients

A retention gradient along a chromatographic column may be advantageously combined with other aspects of this invention. The following discussion is primarily in terms of gas chromatography and retention gradients established through the use of a temperature gradient. It should be understood, however, the general principles apply to other varieties of chromatography and other means of establishing retention gradients.

A negative thermal gradient applied to a gas chromatographic column compresses bands as they move with the carrier gas along the column. The front of a band is always at a lower temperature than the rear of the band and so moves at a lower velocity than the rear band. The band is thus compressed in distance along the column. Chromatographic band broadening processes oppose this thermally driven compression. The band reaches a length along the column determined by a balance of the thermally driven compression and band broadening processes.

A retention gradient along the column may be combined with a retention gradient in time. A negative thermal gradient may be established along a gas chromatographic column such that the outlet end of the column is cooler than the head of the column. The temperature at every point along the column may then be increased at a definite rate as in a gas chromatographic temperature program. The two gradients, in distance and in time, together create an infinitude of moving temperature zones. Any particular temperature has a trajectory on this surface moves from the head of the column to the end of the column as the temperature program proceeds. A sample substance moving along the column driven by a carrier gas, moves toward the trajectory of a particular temperature, the "characteristic focus temperature" of the substance. The existence of this characteristic focus temperature may be demonstrated by performing two thought experiments. In the first, the substance is nearer the head of the column than its characteristic focus temperature and so moves along the column more rapidly than its characteristic focus temperature gradually slowing its migration rate along the column as it approaches its characteristic focus temperature. In the second, the substance is nearer the end of the column than its characteristic focus temperature and so moves along the column more slowly than its characteristic focus temperature gradually increasing its migration rate along the column as its characteristic focus temperature approaches. If the column is long enough, the substance must eventually reach its characteristic focus temperature and then move with the trajectory of that temperature to the end of the column. The value of this characteristic focus temperature for a particular sample substance depends on the ratio of the two thermal gradients along the column and in time, on the linear velocity of the carrier gas, and on the thermodynamics of the sample substance's interaction with the chromatographic stationary phase.

Gas chromatographic efficiency for the separation of substances whose retentions in a column are similar cannot be improved upon (either in terms of time required or in terms of column length required) by applying a thermal gradient method instead of ordinary isothermal gas chromatography. However, if a temperature program is needed anyway because the sample substances cover a wide range of volatilities, then applying a thermal gradient may be both faster and allow use of a shorter column to obtain a given resolution.

Retention gradients may be established along either or both dimensions of a two-dimensional chromatographic separation to improve separation efficiency. A retention gradient may be established along eight or both dimensions of a two-dimensional chromatographic separation to improve separations efficiency. A retention gradient may be established along the final dimension of a two-dimensional chromatographic separation to improve separation efficiency. A retention gradient may be established along the final dimension of a two-dimensional chromatrograph to allow the use of a mobile phase linear velocity substantially higher than that which is reasonable under isothermal operation so that the entire mobile phase flow from the first dimension can be transferred to the second dimension without loss of separation efficiency.

Two-stage thermal modulators may be heated in a manner resembling temperature programming may be similarly improved in efficiency by establishing a thermal gradient or gradients along one or more stages.

A thermal gradient along a chromatographic column or a stage of a thermal modulator may be created by varying the resistance of the thin electrically conductive film applied to the column or stage. The resistance may be varied by varying the thickness of the electrically conductive film. A thermal gradient in time may be created by varying the electric current through the electrically conductive film as a function of time.

Figure 2A:
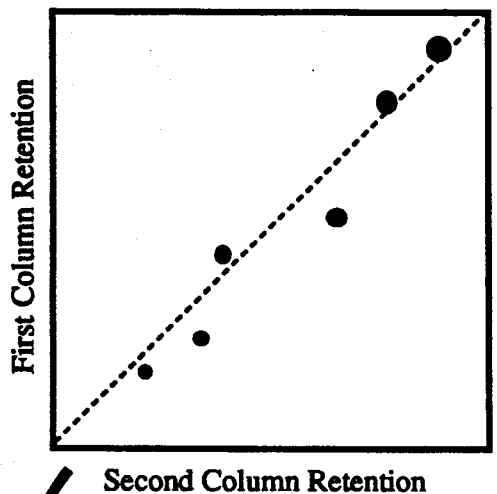
FIGS. 2a-2d show a comparison of four methods of tuning orthogonality of a comprehensive two-dimensional chromatograph.

A method by which such a two dimensional chromatogram could be made orthogonal is illustrated by FIG. 2 which contains several hypothetical two-dimensional chromatograms (as contour plots) Under isothermal conditions a chromatogram like that in FIG. 2A should result. Retentions in the two dimensions correlate strongly because the primary determinate of retention in gas chromatography is volatility, a property of each sample substance, not of the stationary phase. The difference in retention mechanism between primary and secondary columns causes some scatter about the diagonal, but generally, substances strongly retained on one column are also strongly retained on the other. Band durations in FIG. 2A correlate with retention as is normally true in isothermal gas chromatography.

Figure 2B:
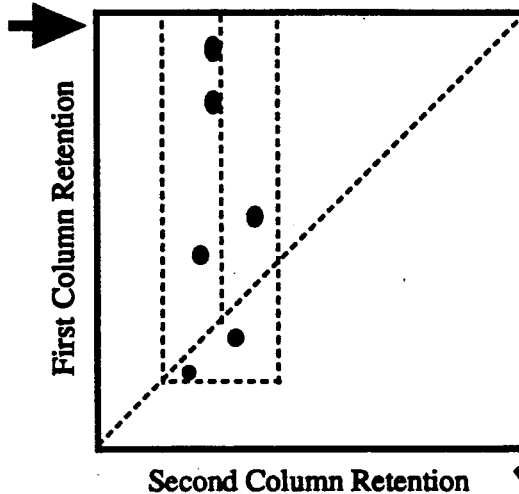

FIG. 2B is a variation of the chromatogram in FIG. 2A. The columns in the array of secondary columns are each at a different temperature starting with a low temperature for the first column in the array and incrementally advancing toward higher temperature for later columns in the array. As the separation proceeds in the first column, sample substances emerging from the primary column are injected into secondary columns which are held at progressively higher temperatures. The temperature increment from column-to-column compensates for the progressively lower volatilities of substances emerging from the primary column as its separation proceeds. Individual chromatograms in the second dimension are still isothermal; they are just not all at the same temperature. This temperature increment from column to column rotates upward the diagonal about which the bands scatter. With an appropriate temperature increment, the diagonal becomes a vertical and the second dimension chromatograms are of nearly uniform duration. The dashed line rectangle delimits the range of accessible retention times. Almost no resolution is lost in the second dimension of chromatography because chromatographic bands are sharper as well as faster eluting.

Figure 2C:
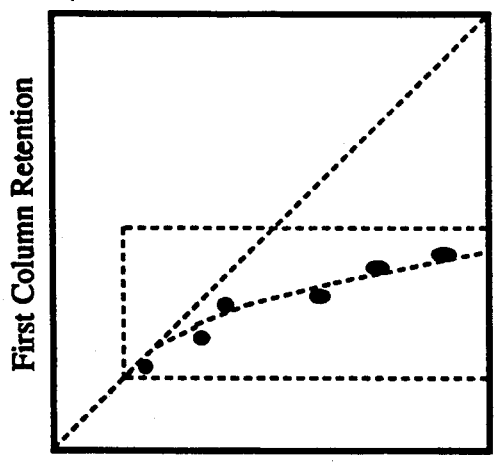

FIG. 2C is another variation of the chromatogram in FIG. 2A. Here, the secondary columns are held at a uniform constant temperature as they were in FIG. 2A, but the primary column is temperature programmed in a conventional way. The increasing temperature of the primary column causes the diagonal about which the bands scatter to curve downward. The dashed line rectangle again delimits the range of accessible retention times. Some resolution is lost in the first dimension because temperature programming is less efficient than isothermal gas chromatography.

Figure 2D:
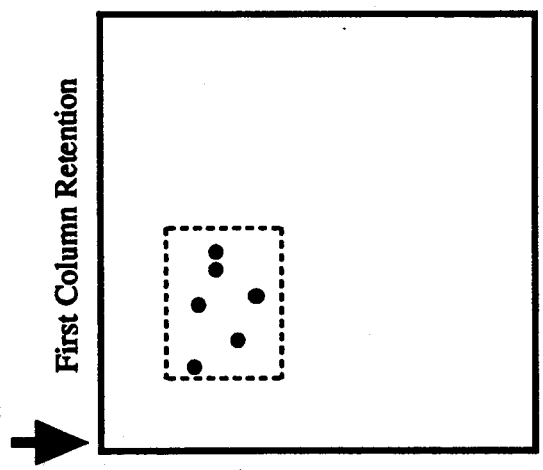

FIG. 2D combines the two effects of temperature variation. The primary column is temperature programmed in a conventional sense while the secondary columns are held at a series of progressively higher temperatures. The bands in this two-dimensional chromatogram are confined to a small portion of the plane originally occupied in FIG. 2A but, within that portion, they are randomly scattered. This technique eliminates correlated retention between the two dimensions giving a much more compact two-dimensional chromatogram.

In the case illustrated by FIG. 2D, incrementing the secondary array temperature from column to column eliminates absolute sample volatility as a contributor to retention on the second column. The dashed vertical line in FIG. 2B is the expected retention time for an "average" substance delivered by the primary column to each secondary column. If a particular substance deviates from the "average" retention for a substance of its volatility on either column, then it will lie off this vertical line in the two-dimensional chromatogram. The placing of a band relative to this line depends on its relative retention on the two columns and not on its absolute volatility. Correlation in retention due to sample volatility is thus eliminated and the two-dimensional gas chromatogram is much more orthogonal.

All chromatographic bands in FIG. 2D fall within a limited and defined range of retention times in the second dimension of chromatography because the two-dimensional separation has been tuned to eliminate retention correlation and maximize orthogonality. The limits of this range in a particular comprehensive two-dimensional chromatogram are determined by the parameters of the chromatographic system such as lengths of columns, linear velocities of carrier gas, and temperatures and by the sample. There is a limit to how much any particular substance can deviate from the average substance in a sample mixture of a given type, and therefore, there is a limit to how much its retention can deviate from the average retention in the second dimension. For example, in a mixture of petroleum hydrocarbons the alkanes provide a lower limit of substance polarity and the aromatics provide an upper limit.

Because retention times in the second dimension of chromatography are limited in range, one column, if sufficiently fast, may be used in place of the array of identical second columns. This single secondary column is recycled to generate every second dimension chromatogram in sequence so as to form a comprehensive two-dimensional chromatogram. By incrementing the temperature of this single secondary column from chromatogram to chromatogram we obtain the same orthogonal separation as in the hypothetical instrument. The structure of FIG. 1 is a practical implementation replacing the hypothetical array of columns.

To orthogonalize a comprehensive two-dimensional chromatographic separation, a parameter affecting retention, such as temperature, of the second column, is varied as a function of progress of the first dimension of chromatography. The variation is done at a rate such that the chromatographic bands emerge from the second column within a limited and defined range of retention times throughout the period of the first dimension chromatogram. As a consequence of this process, retention mechanisms in common between dimensions are eliminated and the comprehensive two-dimensional chromatogram is substantially orthogonal. Choosing a rate of variation of the second column as a function of progress of the first dimension of chromatography is a tuning process which results in orthogonality.

From the foregoing discussion it is clear that an embodiment of the invention may be described as: the method wherein a chromatographic parameter affecting retention of the final dimension of chromatography is varied as a function of the progress of the first dimension of chromatography such that, the final series of bands emerges from the final dimension of chromatography within a limited and defined range of retention times and the comprehensive two-dimensional chromatogram is substantially orthogonal.

In gas chromatography, sample volatility is one retention mechanism in common between dimensions that can be eliminated by this orthogonalization process. The procedure can also eliminate correlations in retention due to any mechanism. Tuning the orthogonality removes any common effects so that subtle differences in retention can be clearly seen. Two dimensions of chromatography that differ even slightly in retention mechanism ca be tuned to generate orthogonal two-dimensional chromatograms. As the two dimensions are made more alike, the tuning process becomes more delicate and results in a chromatogram with lower overall resolution, but the comprehensive two-dimensional chromatogram can still be made orthogonal.

Tuning orthogonality can optimize instrument performance with respect to a particular sample or sample type. For example, a mixture containing substances only in a particular range of volatilities and polarities might crowd into one region of the accessible space but leave another region empty. Tuning the separation can shift the pattern to make more effective use of the chromatographic space. In orthogonalizing the chromatography certain chemical features which sample components may have in common, e.g., volatility, polarizability, and/or polarity, may be suppressed. In this way the system becomes sensitive to subtle chemical differences between sample components.

Orthogonality tuning is also applicable to higher dimensional chromatography.

Temperature is a convenient parameter in tuning the orthogonality of a multi-dimensional gas chromatogram, but any parameter affecting retention may be used with any variety of chromatography. Mobile phase linear velocity may be used with gas, liquid, and supercritical fluid chromatography. It is to be noted that in supercritical liquid chromatography it is possible to "hot trap" samples, that is, to trap a sample by heating a portion of column or phase. This is the reverse of what is therefore usually encountered in gas chromatography. Mobile phase solvent composition may be used with liquid and supercritical fluid chromatography. The various dimensions of a comprehensive multi-dimensional chromatograph may be tuned each using a different adjustable parameter or using the same adjustable parameter.

Combining a retention program on the first dimension of chromatography with an orthogonality tuning on the second dimension of chromatography using the same retention parameter is an especially useful technique. For example, in gas chromatography the second dimension's temperature may increment at the same average rate as the first dimension's temperature program. Similarly, the second dimension of chromatography may have the same rate of mobile phase volumetric flow increase as first dimension's flow program. The second dimension of chromatography may have the same rate of mobile phase solvent composition increase as first dimension's mobile phase solvent composition gradient program.

If at least one additional parameter is available to independently tune retention in one of the two dimensions, then not only can the rates of change be the same on the two dimensions, but the values of the changing retention parameter can be made equal as the retention program proceeds. For example, temperature of the second dimension of chromatography can be the same as a first dimension temperature program. The second dimension is so fast in comparison to the rate of temperature change of the first dimension that the second dimension is essentially isothermal on the time scale of one second dimension separation even if the second dimension is allowed to increase in temperature continuously at the same rate as the first dimension temperature program. Similarly, the mobile phase volumetric flow through the second dimension of chromatography can be the same as a first dimension flow program. Alternatively, the mobile phase solvent composition through the second dimension of chromatography can be the same as a first dimension mobile phase solvent composition gradient program.

In summary, independently tunable parameters include: (a) lengths of the first and final dimensions of chromatography; (b) temperatures of the first and final dimensions of chromatography; (c) mobile phase linear velocities through the first and final dimensions of chromatography; (d) relative stationary phase film thicknesses or loadings in the first and final dimensions of chromatography; (e) rates of change of temperature of the first and final dimensions of chromatography; (f) rates of change of mobile phase linear velocity of the first and final dimensions of chromatography; and (g) rates of change of mobile phase composition of the first and final dimensions of chromatography.

A completely orthogonal two-dimensional chromatogram is one in which no common retention mechanism operates across the dimensions of chromatography. In such a chromatogram, all regions of the retention plane are accessible, chromatographic bands appear to be randomly distributed throughout the retention plane, and statistical measures of scatter are maximized. Complete orthogonality is not always desirable, however. An imperfect tuning may give a quite adequate two-dimensional separation. A particular sample simply may not have any substances to occupy certain regions of the plane even though such regions are accessible and would be occupied by a different sample.

Consider a two-dimensional gas chromatogram for simplicity (it being understood that similar principles can be applied to other types of chromatography and to more than two dimensions of chromatography). A separation may be tuned such that second dimension retention times of a known homologous series, such as the n-alkanes, depend not at all or at most, only weakly, upon first dimension retention times. Second dimension retention times which remain constant as first dimension retention times vary with carbon number in the homologous series are said to be "independent" of first dimension retention times. In gas chromatography for example, this condition of constant second dimension retention times for a given homologous series can be obtained by systematically varying the temperature of the second dimension column as the first dimension separation proceeds. The temperature increases at a rate such that each successive member of the homologous series enters the second column at a temperature that is just enough higher than the temperature at which the previous member of the series entered to force its capacity factor to be equal to that of the previous member of the series. Thus, all members of the homologous series have the same retention time on the second column. If the first dimension column is temperature programmed at the same rate as the rate of temperature increase of the second dimension column, then the members of the homologous series are also evenly spaced in retention on the first dimension column.

Figure 3:
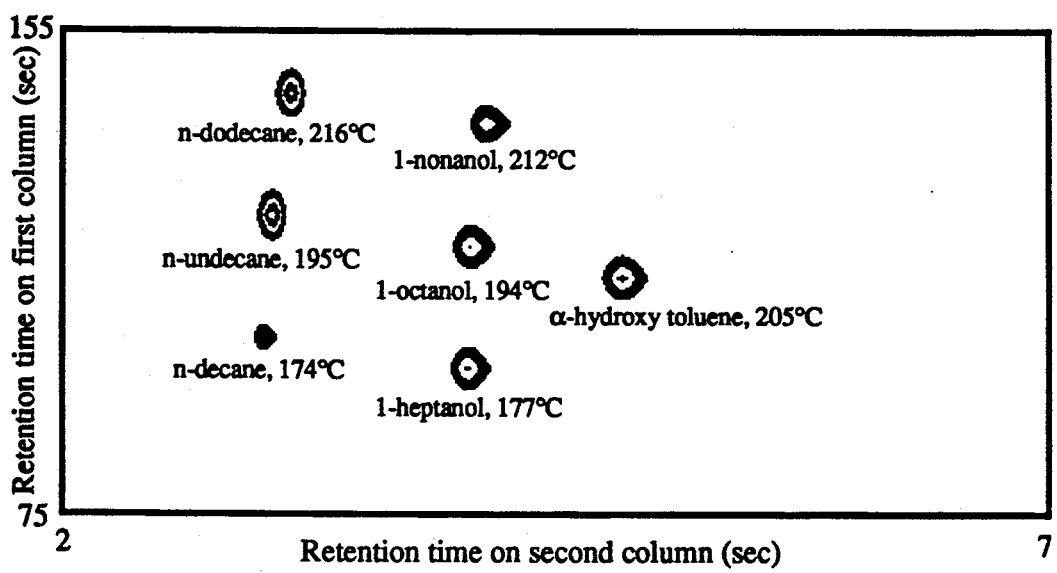
FIG. 3. is an orthogonal comprehensive two-dimensional gas chromatogram.
Figure 4B:
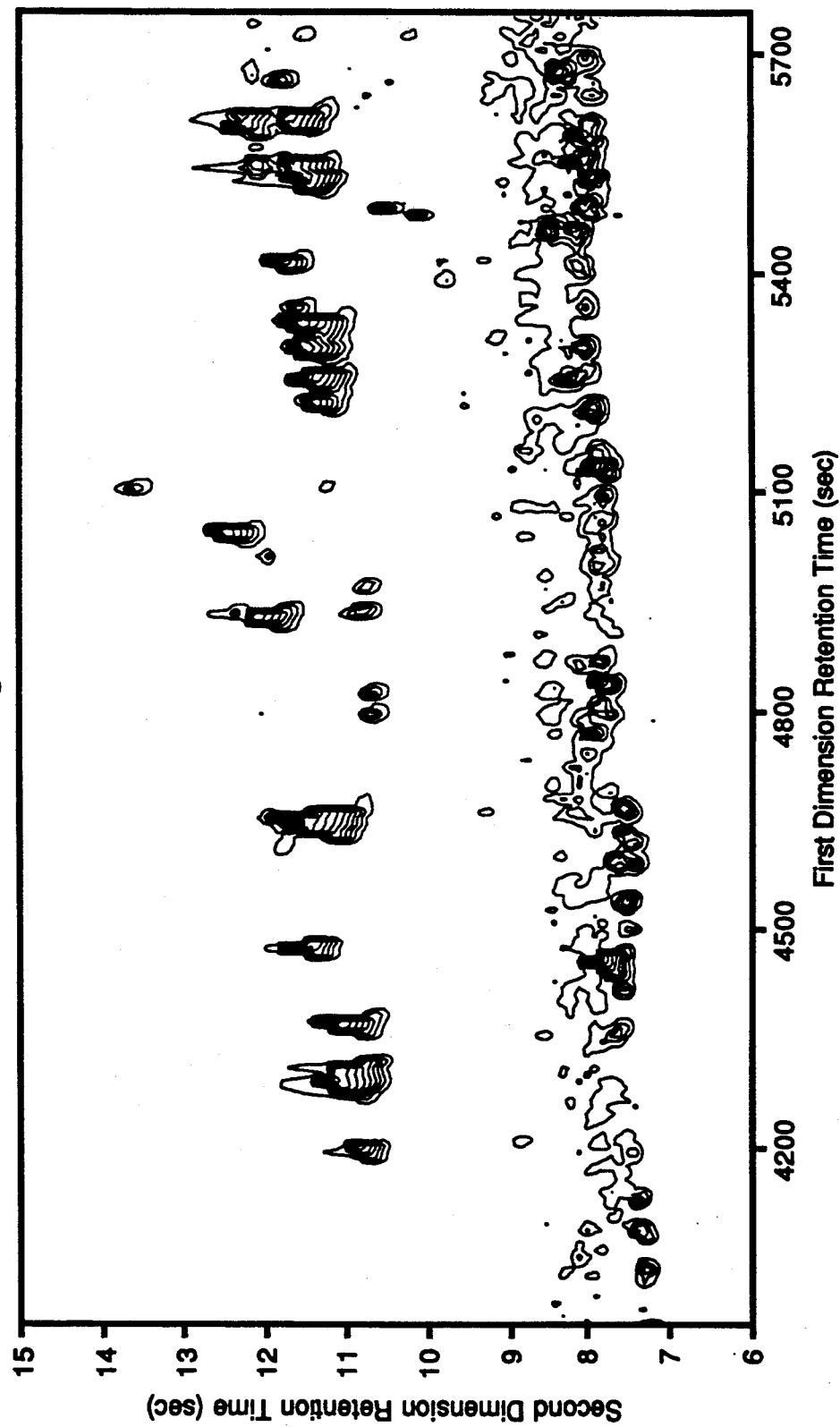
Figure 4C:
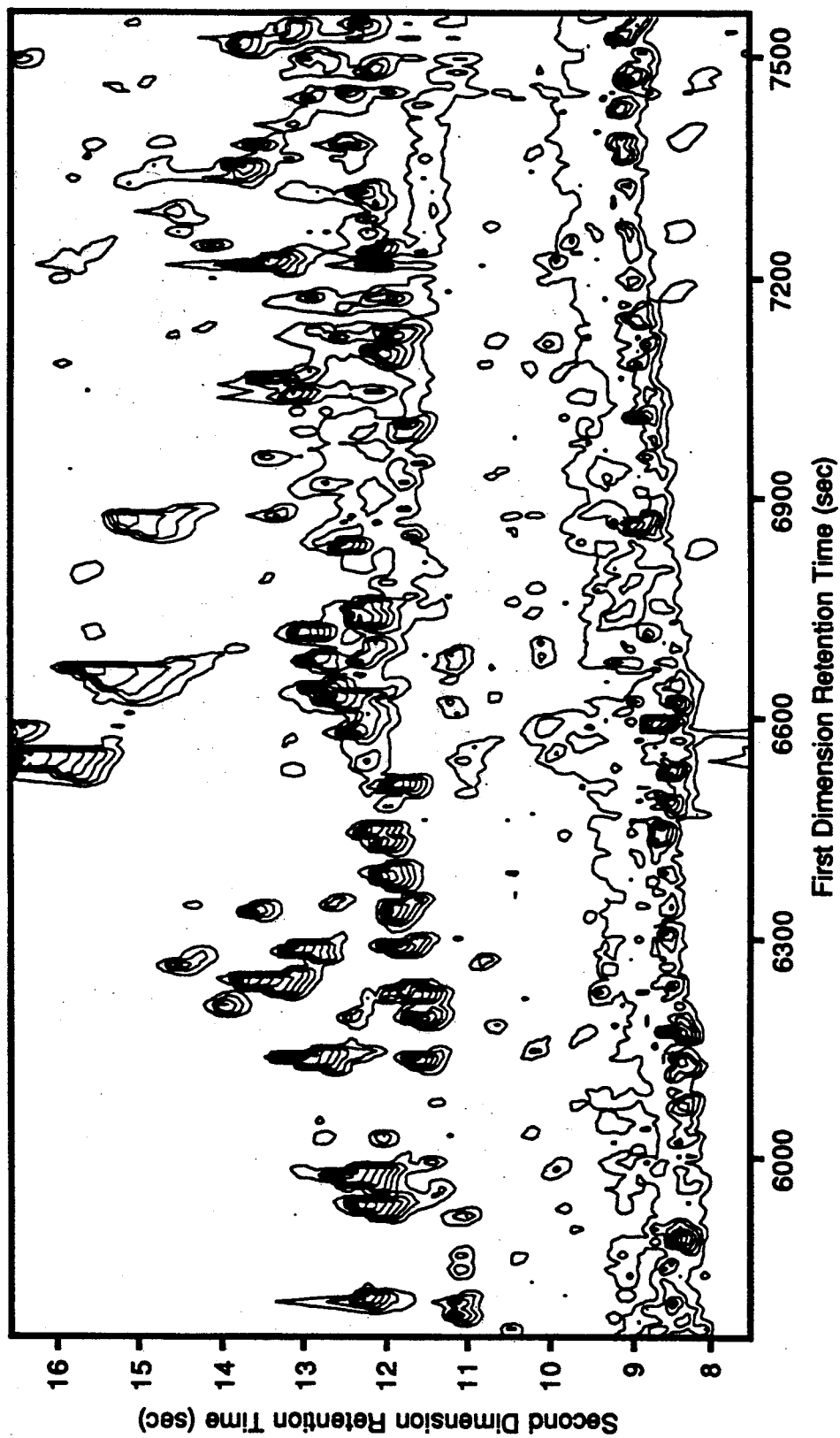
Figure 4D:
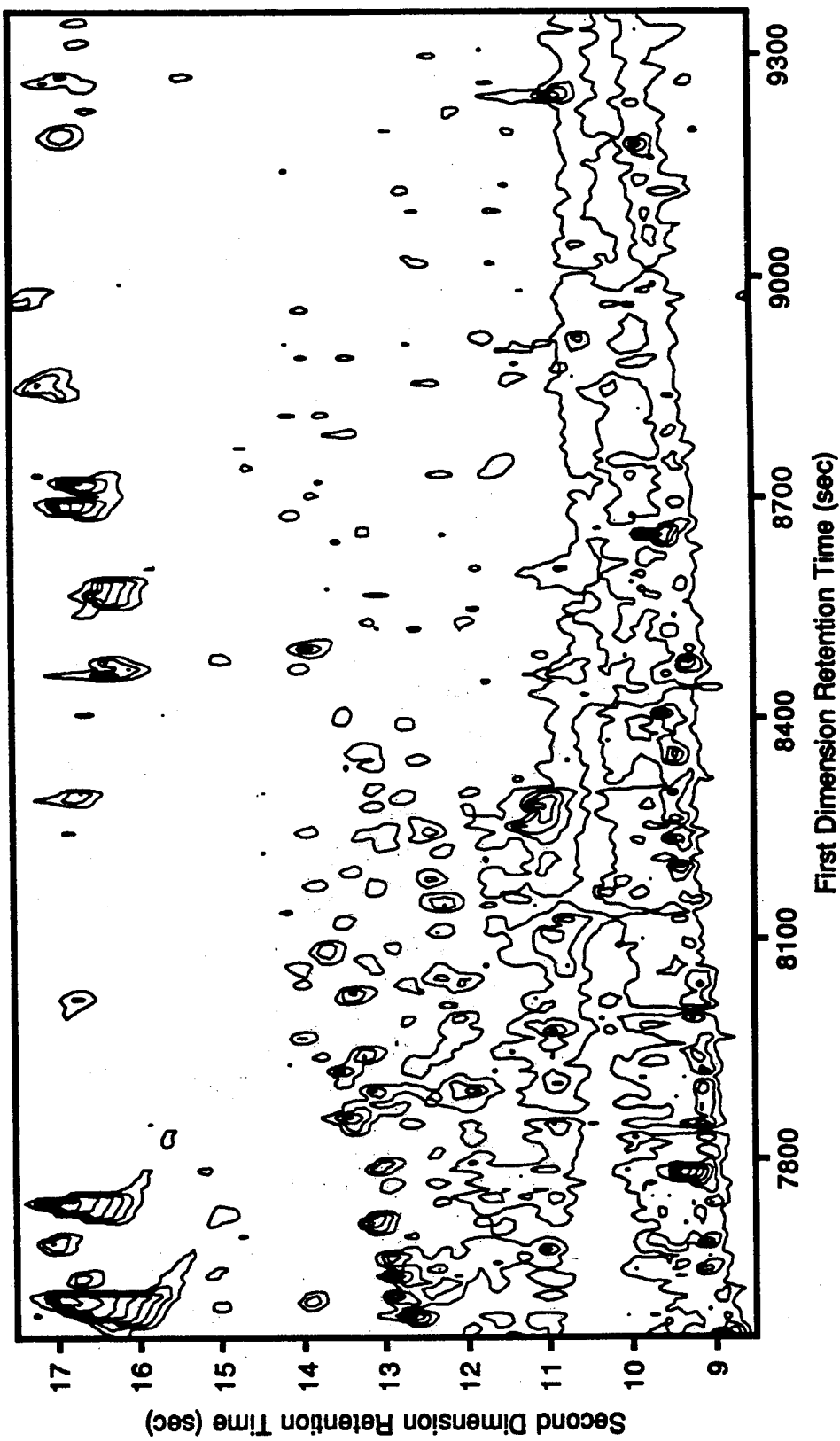
Figure 4E:
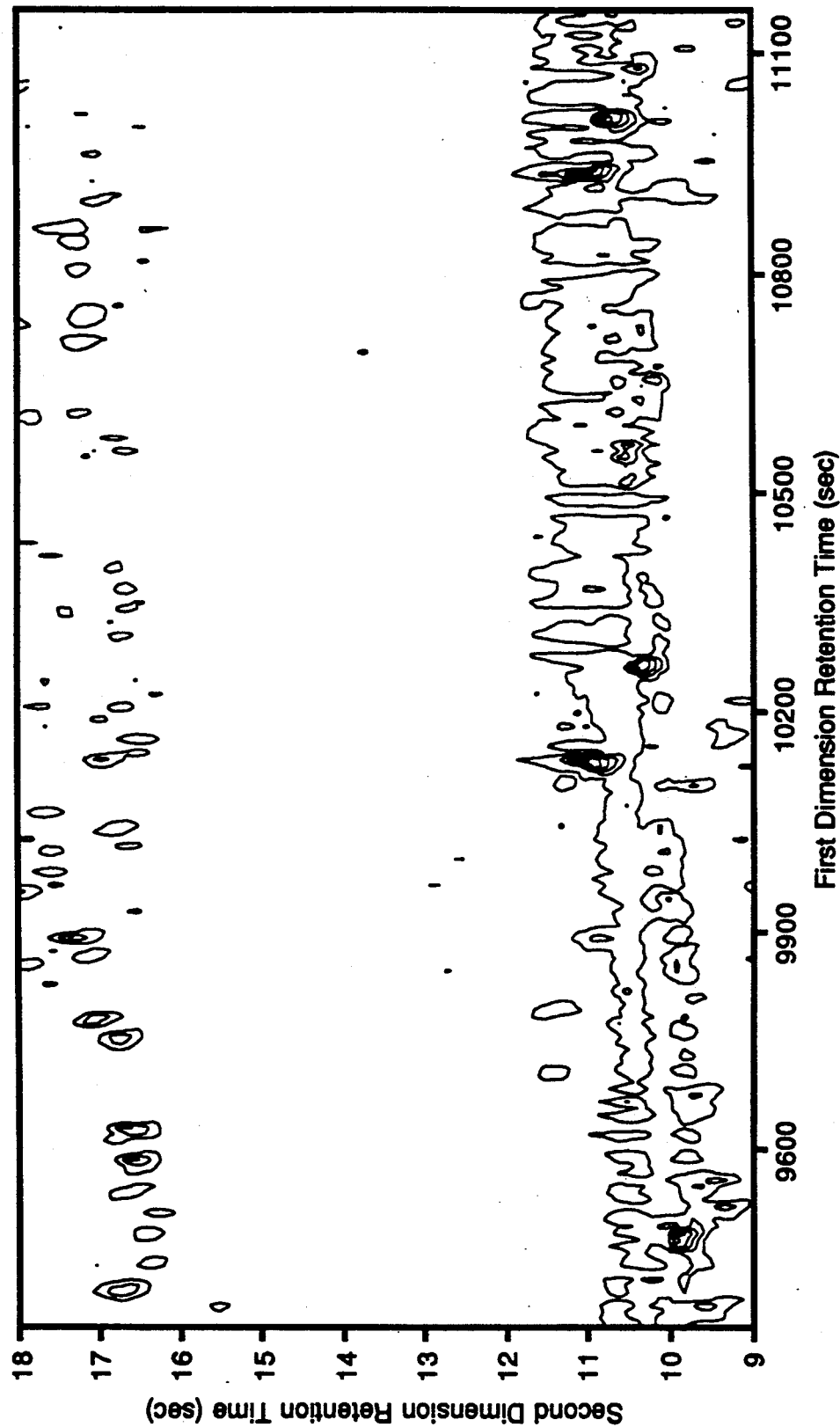

FIG. 3 is an experimental demonstration of orthogonality tuning in gas chromatography. This chromatogram was generated using the instrument shown in FIG. 1. This first column was 11 meters long, 250 micrometers inside diameter, and contained a methyl 5% phenyl silicone stationary phase. The second column was 1.4 meters long, 250 micrometers inside diameter, and contained a OV1701 stationary phase. The carrier gas flow rate through both columns was 2 mL/minute. The oven temperature was initially isothermal at 70° C. for 45 seconds and then increased at a rate of 43° C./minute. Each modulator stage was 6 cm long. Electric current pulses 125 milliseconds in duration were applied to each of the two modulator stages. In addition to the n-alkanes, members of two other homologous series are present. The primary alcohols show the same independence of second dimension retention as the n-alkanes but are shifted to later retention in the second dimension. Alcohols are more polar than alkanes and should be more strongly retained on the polar second stationary phase. With the non-polar first dimension stationary phase, this separation is largely based on volatility in the first dimension and polarity in the second. The members of a given homologous series all have the same polarity (at least over a relatively short part of the series such as in this example) and so all have the same retention in the second dimension. Members of the homologous series differ in volatility, however, and so have different retentions in the first dimension.

The present invention is particularly useful for combining two dimensions of the same type, for example, two gas chromatographic dimensions, two supercritical fluid chromatographic dimensions, or two liquid chromatographic dimensions or even two electrophoretic dimensions. In each of these chromatographic techniques, a retention mechanism in common will exist if the two dimensions are of the same general type. But, to ease interfacing between dimensions and to simplify choice of chromatographic conditions for particular samples, it is desirable to use two dimensions which are quite similar. Tuning the orthogonality of a comprehensive two-dimensional chromatogram eliminates even very strong retention mechanisms in common between the two dimensions of chromatography making the separation obtainable even with two very similar dimensions of chromatography just as orthogonal as with very different dimensions.

The present invention is particularly useful for separating complex mixtures, for example, petroleum samples. FIG. 4 is comprehensive two-dimensional gas chromatogram of a partially evaporated gasoline sample. This chromatogram was generated using the instrument design shown in FIG. 1. The first column was combined from two pieces, the first of these was 50 meters long, 250 micrometers inside diameter, and contained a SE-30 stationary phase, 0.5 micrometer in thickness; the second of these was 50 meters long, 250 micrometers inside diameter, and contained a SE-30 stationary phase, 1.0 micrometer in thickness. The second column was 2.8 meters long, 100 micrometers inside diameter, and contained OV1701 stationary phase, 0.25 micrometer in thickness. The carrier gas linear velocity through the first column was 17 cm/second and through the second column was 212 cm/second. The oven temperature was initially 30° C. and then increased at a rate of 0.8° C./minute. The inlet modulator stage was 12 cm long and the outlet modulator stage was 5 cm long. Electric current pulses 70 milliseconds in duration were applied to the inlet stage and 35 milliseconds in duration were applied to the outlet stage.

Structure of the Two-Stage Thermal Modulator

A two-stage thermal modulator is a piece of tube containing an adsorbent material and having an inlet and an outlet. A carrier fluid flows through the modulator from the inlet to the outlet.

The tube may be a part of a chromatography column externally coated with a thin electrically conductive film or formed from a conductive wall tube. The modulator may be prepared integrally on a part of the chromatography column with other parts of the same piece of column retaining their normal function as chromatographic column or may be prepared on a piece of chromatography column not part of a functioning chromatographic column.

The modulator is divided into two portions. The first portion may be divided into one or more first stages. The second portion is an outlet stage. The stages may be heated sequentially by synchronized electrical current pulses. Electrical current is applied through electrical contacts. At least one electrical contact is made at each junction between modulator stages. A thermal modulator comprising one or more first stages and an outlet stage may be termed either "a two-stage thermal modulator" or "a multi-stage thermal modulator".

The thin electrically conductive film may be composed of gold and have a resistance in the range of 10 ohms per centimeter of column length to 199 ohms per centimeter of column length. Alternatively, the thin electrically conductive film may be composed of a colloidal metal paint and have a resistance in the range of 0.2 ohms per centimeter of column length to 5 ohms per centimeter of column length. Alternatively, commercially available aluminum-clad fused silica open tubular capillary tubes may be used such as those sold by SGE, of Ringwood, Australia, and Quadrex Corporation, New Haven, Conn. Generally, an applied voltage is selected no higher than 240 volts and no lower than one volt and may be either A.C. or D.C. In one embodiment, a low D.C. voltage such as 40 volts is used. A negative thermal gradient may be created along any first stage or the outlet stage of the multi-stage thermal modulator.

The thermal modulator may be enclosed in a controlled temperature enclosure or may be exposed to ambient temperature air. The controlled temperature enclosure may be heated electrically or it may be cooled by a Peltier heat pump or other means of refrigeration.

Operation of a Two-Stage Thermal Modulator

The purpose of a two-stage thermal modulator is to accumulate substances from a flowing carrier fluid and form them into concentration pulses in the same flowing carrier fluid. A substance which can be accumulated and formed into concentration pulses is termed a "retained substance", a "modulatable substance", or simply "sample". Other substances which cannot be accumulated are components of the carrier fluid. A concentration pulse generated by a two-stage thermal modulator has an amplitude or peak concentration proportional to the amount or concentration of modulatable substance entering during a time of accumulation. If the amount of modulatable substance varies from one accumulation time period to another, then the amplitude of the generated concentration pulses also vary and a modulation envelope of the concentration pulse series follows the variation in amount or concentration of modulatable substance.

The operation of a two-stage thermal modulator is best understood with reference to a gas as the carrier fluid and a fused silica capillary gas chromatographic column as the chromatographic column. It should be understood, however, that similar principles apply to the use of other carrier fluids and other forms of chromatography.

Any substances retained by the adsorbent move more slowly through the tube than does the carrier. Applying a temperature pulse to the tube releases any retained substances from the adsorbent allowing them to move at a greater speed through the tube and generates a concentration pulse moving through the tube with the carrier.

Returning to FIG. 1, the first portion of a two-stage thermal modulator 14 accumulates retained substances over a relatively long time from a relatively large volume of carrier. A current pulse applied to the first stage through electrical contacts 26 and 30 connected to the first stage at connections 34 and 32 releases retained substances into the carrier allowing them to flow onto a second stage 16 as a concentration pulse. The second stage may be the outlet stage. If the first portion of a two-stage thermal modulator includes more than one stage, then a current pulse is applied to each such stage in sequence releasing retained substances into the carrier and allowing them to flow onto the next stage until retained substances reach the outlet stage. The outlet stage 16, which is relatively cool at this time, focuses the concentration pulse into a small volume at the beginning of the outlet stag and holds it while the all other stages cool enough to begin accumulating substances again. Heat carried with the fluid onto the outlet stage may form a negative thermal gradient along an initial portion of the outlet stage such that the concentration pulse is focussed into a small distance along the outlet stage. A current pulse applied to the outlet stage through electrical contacts 26 and 30 connected to the outlet stage at connections 34 and 32 raises the temperature of the adsorbent over a period of time so that the concentration pulse accelerates along the outlet stage. The outlet stage is sufficiently long so that the concentration pulse is moving at a speed at least as fast as it will move beyond the end of the outlet stage by the time it reaches the end of the outlet stage. For optimal operation of a two-stage thermal modulator, there should be no further acceleration of the concentration pulse after it exits from the outlet stage.

One embodiment of two-stage thermal modulation may be described as follows: a method of two-stage thermal modulation for generating concentration pulses in a fluid stream flowing through a tube, the tube comprising an inlet, an outlet, a first portion which is a length of the tube comprising a first stage, and a final portion which is a length of the tube comprising a outlet stage, the method comprising the steps of: (a) creating a flow of carrier fluid in a direction through the tube to produce a carrier fluid flow; (b) introducing a sample into the carrier fluid flow, the sample comprising one or more sample substances; (c) positioning the temperature of the first stage such that the sample is retained; (d) positioning the temperature of the outlet stage such that the sample is retained; (e) accumulating within the first stage for a period of time sample substances carried thereinto by the carrier fluid, thus forming a first concentration; (f) positioning the temperature of the first stage to release the first concentration into the carrier fluid flow in the form of a first concentration pulse; (g) carrying the first concentration pulse in the direction of carrier fluid flow toward the outlet stage; (h) accumulating the first concentration pulse at the inlet of the outlet stage so as to focus and hold therein for a period of time, sample substances of the first concentration pulse carried by the carrier fluid, thus forming an outlet concentration more compact in distance than the first concentration pulse; (i) positioning the temperature of the first stage so as to resume accumulating therein for a period of time sample substances carried thereinto by the carrier fluid; (j) positioning the temperature of the outlet stage so as to release the outlet concentration into the carrier fluid flow in the form of an outlet concentration pulse, the outlet concentration pulse being of shorter duration than the first concentration pulse; and (k) positioning the temperature of the outlet stage such that the sample is retained.

Multi-stage thermal modulators have numerous applications. An outlet concentration pulse may be passed through a dimension of chromatography to generate a chromatogram. Multiple outlet concentration pulses may be used to generate multiple chromatograms either of multiple individual samples which may be input to the modulator through a conventional injector or of a flowing sample stream such as from a head-space sampler. This process is particularly useful when the outlet stage is prepared on and integrally contiguous with the chromatographic column used to generate chromatograms. A multi-stage thermal modulator is particularly useful at the junction between dimensions of chromatography in two-dimensional or multi-dimensional chromatography. Outlet concentration pulses may be carried by the carrier fluid directly to a detector. A pulse sensitive detector may synchronize its operation with the arrival of each outlet concentration pulse in the series. By this means, the concentrations of modulatable substances are increased at the detector during its time of operation to improve sensitivity and limit of detection. Some of the detectors which may benefit from this improvement include a flame ionization detector, a thermal conductivity detector, a Fourier transform mass spectrometer, a time-of-flight mass spectrometer, an ion-trap mass spectrometer, an ion mobility spectrometer, an infrared absorbance detector, or an infrared emission detector. A phase-locked loop may be used to observe the signal from such a detector. In one embodiment, the length of chromatographic column used to form the multi-stage modulator is incorporated within a detector assembly so that it becomes an integral part of the detector design and operation. In another embodiment, the length of chromatographic column used to form the multi-stage modulator is prepared on a chromatographic column used for chromatographic separation near the outlet end of the column.

Comprehensive and Orthogonal Two-Dimensional Capillary Electrophoresis

Capillary electrophoresis is not chromatography, but in many ways it is similar to chromatography and produces chemical separations which resemble chromatograms. Consequently, much of this invention applies to capillary electrophoresis, also. One embodiment of the invention is: a method of chemical separation comprising one or more portion of tube forming one or more capillary electrophoretic column, the method further comprising the steps of: (a) injecting a sample composed of two or more substances into a first dimension of electrophoresis; (b) carrying the sample along the first dimension of electrophoresis in a direction so as to cause a first separation of the sample into a first series of bands dispersed during a first separation time period, each band of the first series of bands being composed of one or more substance and being either separated from or partially overlapping with one or more other band in the first series of bands; (c) accumulating a portion of the sample in a modulator positioned between the first dimension of electrophoresis and a final dimension of electrophoresis disposed in serial relationship with the first dimension of electrophoresis; (d) transmitting the portion of the sample from the modulator as a concentration pulse into the final dimension of electrophoresis; (e) carrying the portion of the sample along the final dimension of electrophoresis in a direction so as to cause a final separation of the portion of the sample into a final series of bands dispersed during a final separation time period; and (f) repeating steps (c), (d), and (e) during the first separation time period so as to generate a multiplicity of the concentration pulses, a multiplicity of the final separations and a multiplicity of final series of bands during a multiplicity of final separation time periods such that, the first series of bands emerging from the first dimension of electrophoresis is submitted to and transmitted through the final dimension of electrophoresis with fidelity, the fidelity comprising the maintenance of the first separation in a comprehensive two-dimensional electrophorogram created from the multiplicity of the final series of bands, the comprehensive two-dimensional electrophorogram being a separation of the sample into a set of bands dispersed on a retention plane, the retention plane being a vectorial space of dimension two and spanned by the first and final separation time periods, and an electrophoretic parameter affecting retention of the final dimension of electrophoresis is varied as a function of the progress of the first dimension of electrophoresis such that, the final series of bands emerges from the final dimension of electrophoresis within a limited and defined range of retention times and the comprehensive two-dimensional electrophorogram is substantially orthogonal.

The invention may be more fully understood with reference to the accompanying drawings and the following description of the embodiments. The invention is not limited to the exemplary embodiments but should be recognized as contemplating all modifications within the skill of an ordinary artisan.

What is claimed is:

1. A method of chemical separation within one or more portion of tube forming one or more chromatographic column, said method comprising the steps of:
    (a) injecting a sample composed of two or more substances into a first dimension of chromatography;
    (b) carrying said sample along said first dimension of chromatography in a direction so as to cause a first separation of said sample into a first series of bands dispersed during a first separation time period, each band of said first series of bands being composed of one or more substance and being either separated from or partially overlapping with one or more other band in said first series of bands;
    (c) accumulating a portion of the sample in a modulator positioned between said first dimension of chromatography and a final dimension of chromatography disposed in serial relationship with said first dimension of chromatography;
    (d) transmitting said portion of the sample from said modulator as a concentration pulse into said final dimension of chromatography;
    (e) carrying said portion of the sample along said final dimension of chromatography in a direction so as to cause a final separation of said portion of the sample into a final series of bands dispersed during a final separation time period; and
    (f) repeating steps (c), (d), and (e) during said first separation time period so as to generate a multiplicity of said concentration pulses, a multiplicity of said final separations and a multiplicity of said final series of bands during a multiplicity of said final separation time periods such that, said concentration pulses are generated at a rate faster than one every thirty seconds, said multiplicity of final separations comprises more than ten said final separations in a single chemical separation, and said first series of bands emerging from said first dimension of chromatography is submitted to and transmitted through said final dimension of chromatography with fidelity.

2. The method according to claim 1, wherein said first dimension of chromatography and said final dimension of chromatography comprise any combination of gas, supercritical fluid, or liquid chromatographic mobile phases.

3. The method according to claim 1, wherein said modulator comprises a single-stage thermal modulator.

4. The method according to claim 1, wherein said modulator comprises a multi-stage thermal modulator.

5. The method according to claim 1, wherein said modulator comprises a cold trap.

6. The method according to claim 1, wherein said modulator comprises an injection valve with a sample loop.

7. The method according to claim 1, wherein said modulator comprises a thermal modulator and is prepared integrally on the same portion of tube as said final dimension of chromatography.

8. The method according to claim 1, wherein said concentration pulse is transmitted to said final dimension of chromatography before a previous said portion of the sample has completely eluted from said final dimension of chromatography and more than one said portion of the sample is present in said final dimension of chromatography at one time.

9. The method according to claim 1, wherein one or more dimension of chromatography is serially disposed between said first dimension of chromatography and said final dimension of chromatography with two or more junctions created between the dimensions of chromatography, each said junction having a prior dimension of chromatography and a subsequent dimension of chromatography such that, at each said junction, sample emerges from said prior dimension of chromatography as a series of bands, a multiplicity of portions of said sample are accumulated by an instance of said modulator and are transmitted to the subsequent dimension of chromatography so as to generate a multiplicity of concentration pulses and a multiplicity of subsequent dimension separations with fidelity, said fidelity comprising maintenance of all prior dimension separations such that, a comprehensive multi-dimensional chromatogram is created from a multiplicity of a series of bands emerging from said final dimension of chromatography, said comprehensive multi-dimensional chromatogram being a separation of the sample into a set of bands dispersed in a retention space, said retention space being a vectorial space of dimension equal to said multiplicity of dimensions of chromatography and spanned by the separation time periods of said multiplicity of dimensions of chromatography.

10. The method according to claim 1, wherein the entire sample is submitted to both said dimensions of chromatography.

11. The method according to claim 1, wherein a portion of the flow of sample is diverted near a junction between said first and said final dimensions of chromatography such that said portion does not enter said final dimension of chromatography.

12. The method according to claim 1, wherein one or more portions from one or more of said multiplicity of said final series of bands is collected to effect separation of one or more substances from said sample.

13. The method according to claim 1, wherein said multiplicity of final series of bands form a single concatenated and continuous series of bands at an inlet to a detector and said detector transduces said continuous series of bands to form an electronic signal.

14. The method according to claim 13, wherein said electronic signal is displayed as a comprehensive two-dimensional chromatogram with a retention parameter of the first column comprising one axis, a retention parameter of the final column comprising a final axis and signal intensity comprising a third axis.

15. The method according to claim 13, wherein a region occupied by a two-dimensional chromatographic band is integrated on the two-dimensional plane to give a measure of band size.

16. The method according to claim 15, wherein said measure of band size is corrected for a background offset by subtracting the integral computed over a region of equal size to said region located within a distance of ten band durations in any direction from said two-dimensional chromatographic band in the two-dimensional plane.

17. The method according to claim 1, further comprising a retention gradient along one or more of dimensions of chromatography.

18. The method according to claim 17, wherein said retention gradient comprises a stationary phase loading or film thickness gradient.

19. The method according to claim 17, wherein said retention gradient comprises a thermal gradient.

20. The method according to claim 19, wherein said thermal gradient is established by conducting an electric current through a resistive film, the resistance of said film being varied with distance along one or more of said chromatographic columns.

21. The method according to claim 1, wherein said first dimension of chromatography comprises a first stationary phase and said final dimension of chromatography comprises a final stationary phase, said final stationary phase being serially disposed relative to and chemically distinct from said first stationary phase.

22. The method according to claim 21, wherein said first and final dimensions of chromatography comprise serially connected columns containing said first and final stationary phases.

23. The method according to claim 21, wherein said first and final dimensions of chromatography comprise one column containing said first and final stationary phases.

24. The method according to claim 1, wherein said first and said final dimensions of chromatography comprise one chemically uniform stationary phase with a difference in retention mechanism between said first and said final dimensions of chromatography being due to a difference in environment of said first and said final dimensions of chromatography.

25. The method according to claim 24, wherein said difference in environment is a difference in temperature at which sample substances propagate along said first and final dimensions of chromatography.

26. The method according to claim 1, wherein at least one of said first and final dimensions of chromatography comprises a capillary column.

27. The method according to claim 1, wherein a chromatographic parameter affecting retention of said final dimension of chromatography is varied as a function of the progress of said first dimension of chromatography such that, said final series of bands emerges from said final dimension of chromatography within a limited and defined range of retention times and said comprehensive two-dimensional chromatogram is substantially orthogonal.

28. The method according to claim 27, wherein a statistical measure of peak scatter is substantially maximized and the peak capacity of the chromatographic system approximates the arithmetic product of the individual peak capacities of said first and said final dimensions of chromatography.

29. The method according to claim 27, wherein a delay time between generation of said concentration pulse and observation of said final series of bands is used to determine the rate at which said chromatographic parameter affecting retention of said final dimension of chromatography is varied.

30. The method according to claim 27 wherein a signal from a detector placed a part way into said final dimension of chromatography determines the rate at which said chromatographic parameter affecting retention of said final dimension of chromatography is varied.

31. The method according to claim 27, wherein said first and final dimensions of chromatography comprise a gas mobile phase.

32. The method according to claim 31, wherein said chromatographic parameter affecting retention of said final dimension of chromatography is a linear velocity of said gas mobile phase through said final dimension of chromatography and said linear velocity is varied by varying gas pressure applied to a point near a junction between said first and final dimensions of chromatography.

33. The method according to claim 31, wherein said chromatographic parameter affecting retention of said final dimension of chromatography is a linear velocity of said gas mobile phase through said final dimension of chromatography and said linear velocity is varied by varying gas pressure applied to a point near an outlet of said final dimensions of chromatography.

34. The method according to claim 31, wherein said first dimension of chromatography comprises a nonpolar column and said final dimension of chromatography comprises a polar column such that retention in said first dimension of chromatography is substantially determined by volatility of said substances and retention in said final dimension of chromatography is substantially determined by polarity of said substances.

35. The method according to claim 27, wherein said first and final dimensions of chromatography comprise a supercritical fluid mobile phase.

36. The method according to claim 27, wherein said first and final dimensions of chromatography comprise a liquid mobile phase.

37. The method according to claim 27, wherein said chromatographic parameter affecting retention is temperature of said final dimension of chromatography and said temperature is varied as a function of progress of said first dimension of chromatography.

38. The method according to claim 37, wherein said temperature of said final dimension of chromatography is varied at the same rate as a temperature program applied to said first dimension of chromatography.

39. The method according to claim 38, wherein said first and final dimensions of chromatography have the same temperatures at every time during said temperature program.

40. The method according to claim 27, wherein said chromatographic parameter affecting retention is mobile phase linear velocity through said final dimension of chromatography and said mobile phase linear velocity is varied as a function of the progress of said first dimension of chromatography.

41. The method according to claim 40, wherein said mobile phase linear velocity through said final dimension of chromatography is varied at the same rate as a mobile phase linear velocity flow program applied to said first dimension of chromatography.

42. The method according to claim 41, wherein said first and final dimensions of chromatography have the same mobile phase volumetric flow at every time during said flow program.

43. The method according to claim 27, wherein said chromatographic parameter affecting retention is mobile phase solvent composition through said final dimension of chromatography and said mobile phase solvent composition is varied as a function of the progress of said first dimension of chromatography.

44. The method according to claim 43, wherein said mobile phase solvent composition through said final dimension of chromatography is varied at the same rate as a mobile phase solvent composition gradient program applied to said first dimension of chromatography.

45. The method according to claim 44, wherein said first and final dimensions of chromatography have the same mobile phase solvent composition at every time during said mobile phase solvent composition gradient program.

46. The method according to claim 27, wherein one or more of a set of tunable parameters are adjusted such that said orthogonality of said comprehensive two-dimensional chromatogram is maximized, said set of tunable parameters comprising:
  (a) lengths of said first and final dimensions of chromatography;
  (b) temperatures of said first and final dimensions of chromatography;
  (c) mobile phase linear velocities through said first and final dimensions of chromatography;
  (d) relative stationary phase film thicknesses or loadings in said first and final dimensions of chromatography;
  (e) rates of temperature change of said first and final dimensions of chromatography;
  (f) rates mobile phase linear velocity change of said first and final dimensions of chromatography; and
  (g) rates of mobile phase composition change of said first and final dimensions of chromatography.

47. The method according to claim 1, wherein said concentration pulse has a length along and a duration entering said final dimension of chromatography, and furthermore, retention in said modulator is varied as a function of progress of said first dimension of chromatography such that said multiplicity of concentration pulses has substantially constant length and duration.

48. The method according to claim 47, wherein a signal phase relationship between electric current pulses applied to two or more stages of said thermal modulator is varied as a function of progress of the said first dimension of chromatography.

49. The method according to claim 47, wherein an electric current pulse magnitude applied to said thermal modulator is varied as a function of progress of the said first dimension of chromatography.

50. The method according to claim 47, wherein an electric current pulse duration applied to said thermal modulator is varied as a function of progress of the said first dimension of chromatography.

51. The method according to claim 47, wherein temperature of an enclosure containing said thermal modulator is varied as a function of progress of the said first dimension of chromatography.

52. The method according to claim 1, wherein a substance in said final series of bands has greater concentration than said substance in said first series of bands.

53. A method of two-stage thermal modulation for generating concentration pulses in a fluid stream flowing through a tube, said tube comprising an inlet, an outlet, a first portion which is a length of said tube comprising a first stage, and a final portion which is a length of said tube comprising a outlet stage, said method comprising the steps of:
  (a) creating a flow of carrier fluid in a direction through said tube to produce a carrier fluid flow;
  (b) introducing a sample into the carrier fluid flow, said sample comprising one or more sample substances;
  (c) manipulating the temperature of the first stage to cause the sample to be retained;
  (d) manipulating the temperature of the outlet stage such that the sample is retained;
  (e) accumulating within the first stage for a period of time sample substances carried thereinto by the carrier fluid, thus forming a first concentration;
  (f) manipulating the temperature of the first stage to release the first concentration into the carrier fluid flow in the form of a first concentration pulse;
  (g) carrying the first concentration pulse in said carrier fluid flow toward said outlet stage;
  (h) accumulating said first concentration pulse at an inlet of said outlet stage so as to focus and hold therein for a period of time, sample substances of said first concentration pulse carried by the carrier fluid, thus forming an outlet concentration more compact in distance than said first concentration pulse;
  (i) positioning the temperature of the first stage so as to resume accumulating therein for a period of time sample substances carried thereinto by the carrier fluid;
  (j) positioning the temperature of the outlet stage so as to release said outlet concentration into the carrier fluid flow in the form of an outlet concentration pulse, said outlet concentration pulse being of shorter duration than said first concentration pulse; and
  (k) positioning the temperature of the outlet stage such that the sample is retained.

54. The method according to claim 53, further comprising carrying the outlet concentration pulse through the tube so that the outlet concentration pulse emerges at the outlet of the tube, and detecting sample substances in the outlet concentration pulse emerging from the tube.

55. The method according to claim 53, wherein said first portion comprises more than one stage.

56. The method according to claim 53, wherein sample is retained at relatively cool temperature and released at relatively warm temperature.

57. The method according to claim 53, wherein sample is retained at relatively warm temperature and released at relatively cool temperature.

58. The method according to claim 53, further comprising separating said outlet concentration pulse into bands by chromatography.

59. The method according to claim 53, wherein steps (e) through (k) are repeated during the flow of sample through the tube so as to produce a series of thermal modulations providing a series of outlet concentration pulses.

60. The method according to claim 59, wherein said series of outlet concentration pulses forms a modulation envelope that follows a variation as a function of time of said sample.

61. The method according to claim 59, further comprising carrying said series of outlet concentration pulses through a dimension of chromatography.

62. The method according to claim 61, wherein said dimension of a chromatography is prepared in a tube and said outlet stage is prepared on and integrally contiguous with said tube.

63. The method according to claim 59, further comprising:
 (a) detecting with a pulse sensitive detector sample substances in said outlet concentration pulse emerging from the outlet of said tube; and
 (b) synchronizing arrival of each pulse in said series of outlet concentration pulses with the operation of said pulse sensitive detector.

64. The method according to claim 63, wherein a chemical analysis using said detector with said method has improved sensitivity and improved limit of detection over using said detector without said method.

65. The method according to claim 63, wherein said pulse sensitive detector is any one of a flame ionization detector, a thermal conductivity detector, a Fourier transform mass spectrometer, a time-of-flight mass spectrometer, an ion-trap mass spectrometer, an ion mobility spectrometer, an infrared absorbance detector, or an infrared emission detector.

66. The method according to claim 63, wherein a signal emerging from said pulse sensitive detector is observed using a phase-locked loop.

67. The method according to claim 59 wherein said tube is a length of chromatographic column incorporated within a detector assembly.

68. The method according to claim 59 wherein said tube is a portion of a chromatographic column near an outlet end of said column.

69. The method according to claim 53, wherein said first stage and said outlet stage comprise a capillary tube containing a stationary phase suitable for retaining sample substances.

70. The method according to claim 69, wherein said capillary tube comprises an external resistive coat and wherein at least one of said first stage and said outlet stage is heated by passing electric current through said external resistive coat.

71. The method according to claim 69, wherein said capillary tube comprises a conductive wall and wherein at least one of said first stage and said outlet stage is heated by passing electric current through said conductive wall.

72. The method according to claim 53, wherein at least one of said first stage and said outlet stage is cooled by ambient temperature air.

73. The method according to claim 53, wherein at least one of said first stage and said outlet stage is cooled by air in a temperature controlled enclosure.

74. The method according to claim 53, wherein said outlet stage generates multiple outlet concentration pulses by chromatography along said outlet stage so as to separate substances in a mixture.

75. A method of chemical separation comprising one or more portion of tube forming one or more capillary electrophoretic column, said method further comprising the steps of:
 (a) injecting a sample composed of two or more substances into a first dimension of electrophoresis;
 (b) carrying said sample along said first dimension of electrophoresis in a direction so as to cause a first separation of said sample into a first series of bands dispersed during a first separation time period, each band of said first series of bands being composed of one or more substance and being either separated from or partially overlapping with one or more other band in said first series of bands;
 (c) accumulating a portion of the sample in a modulator positioned between said first dimension of electrophoresis and a final dimension of electrophoresis disposed in serial relationship with said first dimension of electrophoresis;
 (d) transmitting said portion of the sample from said modulator as a concentration pulse into said final dimension of electrophoresis;
 (e) carrying said portion of the sample along said final dimension of electrophoresis in a direction so as to cause a final separation of said portion of the sample into a final series of bands dispersed during a final separation time period; and
 (f) repeating steps (c), (d), and (e) during said first separation time period so as to generate a multiplicity of said final separations and a multiplicity of said final series of bands during a multiplicity of said final separation time periods such that,
 said first series of bands emerging from said first dimension of electrophoresis is submitted to and transmitted through said final dimension of electrophoresis with fidelity, and
 an electrophoretic parameter affecting retention of said final dimension of electrophoresis is varied as a function of the progress of said first dimension of electrophoresis such that, said final series of bands emerges from said final dimension of electrophoresis within a limited and defined range of retention times and said comprehensive two-dimensional electrophorogram is substantially orthogonal.

76. A method of two-dimensional chromatographic separation comprising the steps of:
 (a) injecting a sample composed of various sample substances into a first dimension of chromatographic separation;
 (b) carrying said sample along said first dimension of chromatographic separation so as to cause a first resolution of said sample into a series of bands;
 (c) accumulating a portion of the sample between said first dimension of chromatographic separation and a second dimension of chromatographic separation disposed in serial relationship with said first dimension of chromatographic separation;
 (d) transmitting the accumulated portion of sample as a sharp wave front to an inlet of the second dimension of chromatographic separation;

(e) carrying the portion of sample along the second dimension of chromatographic separation so as to cause a further resolution of said portion of sample;

repeating steps (c), (d), and (e) so as to generate a multiplicity of said sharp wave fronts and a multiplicity of said further resolutions by said second dimension of chromatographic separation, without materially changing said first resolution; and detecting said multiplicity of further resolutions so as to generate a multiplicity of second dimension chromatograms together comprising a two-dimensional chromatogram of said sample.

* * * * *